United States Patent
Hirata et al.

(10) Patent No.: US 10,617,361 B2
(45) Date of Patent: Apr. 14, 2020

(54) CASING OF IMPLANTABLE DEVICE AND IMPLANTABLE DEVICE, METHOD FOR MANUFACTURING CASING OF IMPLANTABLE DEVICE, AND METHOD FOR SUPPORTING TREATMENT USING IMPLANTABLE DEVICE

(71) Applicant: Osaka University, Osaka (JP)

(72) Inventors: Masayuki Hirata, Osaka (JP); Toshiki Yoshimine, Osaka (JP); Kojiro Matsushita, Osaka (JP); Tetsu Goto, Osaka (JP); Takufumi Yanagisawa, Osaka (JP); Takafumi Suzuki, Tokyo (JP); Shinichi Yoshimura, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/251,577

(22) Filed: Aug. 30, 2016

(65) Prior Publication Data
US 2017/0049398 A1 Feb. 23, 2017

Related U.S. Application Data

(63) Continuation-in-part of application No. 13/510,841, filed as application No. PCT/JP2011/001402 on Mar. 10, 2011, now abandoned.

(30) Foreign Application Priority Data

Nov. 9, 2010 (JP) .................. 2010-250464

(51) Int. Cl.
*A61N 1/05* (2006.01)
*A61B 5/00* (2006.01)
(Continued)

(52) U.S. Cl.
CPC .......... *A61B 5/6868* (2013.01); *A61B 5/0478* (2013.01); *A61F 2/2875* (2013.01);
(Continued)

(58) Field of Classification Search
CPC ........................... A61N 1/0531; A61N 1/0539
See application file for complete search history.

(56) References Cited

U.S. PATENT DOCUMENTS 7,195,645 B2    3/2007  DiSilvestro et al.
7,346,391 B1 *  3/2008  Osorio ................ A61B 5/0476
                                                          600/378
(Continued)

FOREIGN PATENT DOCUMENTS

JP    2007-530082    1/2007
JP    2009-202020    9/2009
JP    2010-172667    8/2010

*Primary Examiner* — Eric D. Bertram
(74) *Attorney, Agent, or Firm* — Knobbe Martens Olson & Bear, LLP

(57) ABSTRACT

To allow an implantable device including an electronic circuit to be implanted in the head in a more preferable manner in terms of appearance and safely. This implantable device is used for a brain-machine interface or the like. A casing of an implantable device configured to be implanted in a human head has an outer convexity surface matching an external shape of a resected skull related to at least a craniotomy site of the artificial bone designed in accordance with a skull shape of each person in order to fill the craniotomy site. That is, the outer convexity surface of the artificial bone is provided with two functions: the original function of filling the craniotomy site as the artificial bone and a function of serving as the casing of the implantable device.

4 Claims, 24 Drawing Sheets

(51) Int. Cl.
  *A61B 5/0478* (2006.01)
  *A61F 2/28* (2006.01)
  *G06F 3/01* (2006.01)
  *A61N 1/375* (2006.01)

(52) U.S. Cl.
  CPC ........... *A61N 1/0531* (2013.01); *A61N 1/375* (2013.01); *G06F 3/015* (2013.01); *A61B 2562/164* (2013.01); *A61B 2562/166* (2013.01); *A61B 2562/222* (2013.01)

(56) References Cited

U.S. PATENT DOCUMENTS

| | | | |
|---|---|---|---|
| 8,315,686 B2* | 11/2012 | Llinas | A61B 5/0478 600/378 |
| 2005/0075680 A1* | 4/2005 | Lowry | A61N 1/0531 607/45 |
| 2006/0173522 A1* | 8/2006 | Osorio | A61B 5/6864 607/116 |
| 2007/0161919 A1* | 7/2007 | DiLorenzo | A61B 5/04001 600/544 |
| 2008/0215112 A1 | 9/2008 | Firlik et al. | |
| 2009/0124965 A1* | 5/2009 | Greenberg | A61N 1/0531 604/67 |
| 2012/0109252 A1* | 5/2012 | Beuter | A61N 1/36082 607/45 |

* cited by examiner

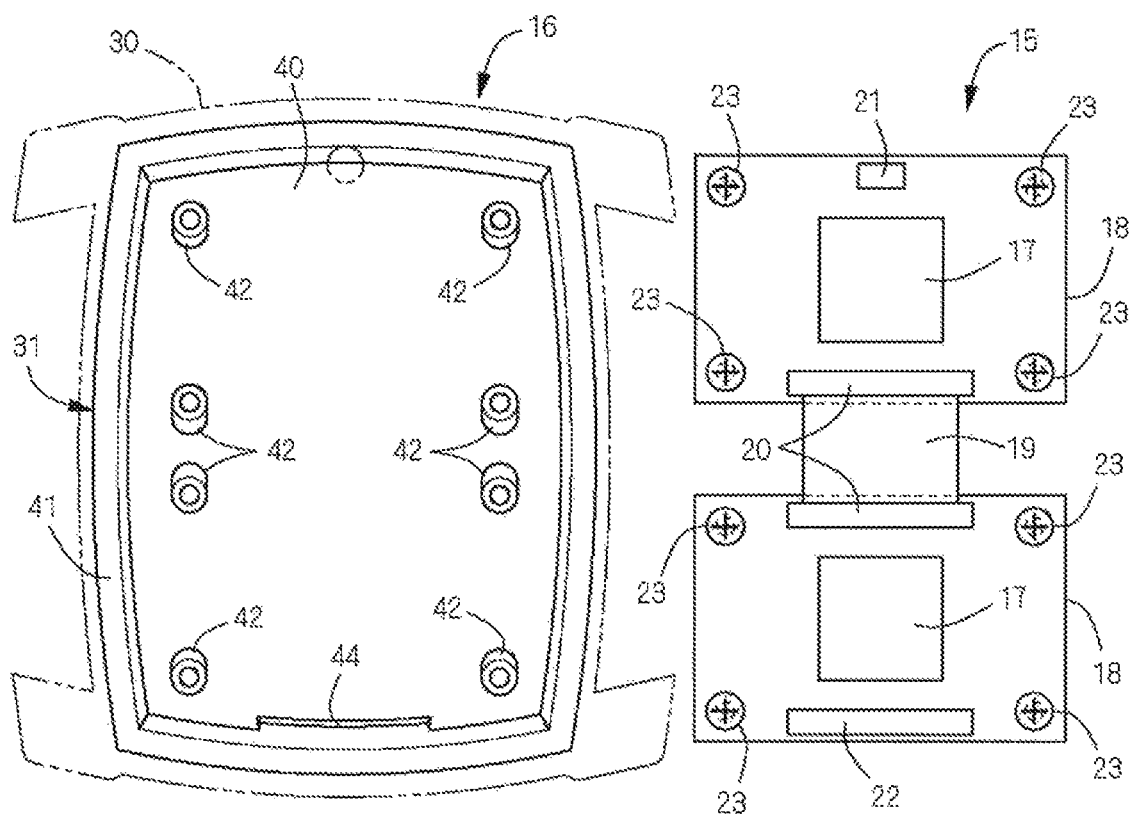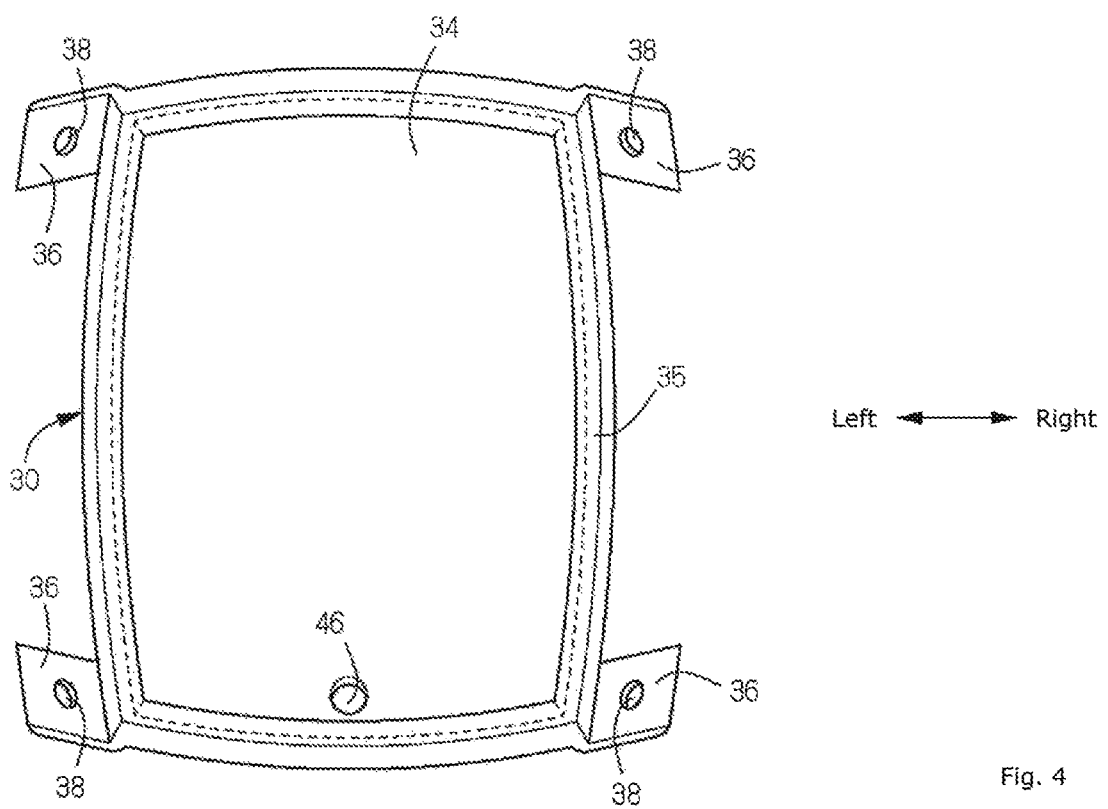
Fig. 4

CASING OF IMPLANTABLE DEVICE AND IMPLANTABLE DEVICE, METHOD FOR MANUFACTURING CASING OF IMPLANTABLE DEVICE, AND METHOD FOR SUPPORTING TREATMENT USING IMPLANTABLE DEVICE

CROSS REFERENCE TO RELATED APPLICATIONS

This application is a continuation-in-part application of and claims the benefit and priority to U.S. patent application Ser. No. 13/510,841, filed on Oct. 4, 2012, which claims the benefit and priority to and is a U.S. National Phase Application of PCT International Application Number PCT/JP2011/001402, filed on Mar. 10, 2011, designating the United States of America, which is an International Application of and claims the benefit of priority to Japanese Patent Application No. 2010-250464, filed on Nov. 9, 2010. The disclosures of the above-referenced applications are hereby expressly incorporated by reference in their entireties.

BACKGROUND OF THE INVENTION

Field

The present invention relates to a casing of an implantable device configured to be implanted in a human body and an implantable device, a method for manufacturing a casing of an implantable device, and a method for supporting treatment using an implantable device.

Description of the Related Art

With the progress of brain-machine interfaces, various types of implantable devices for performing such as acquisition of body information have been developed. Various ideas have been implemented in the casing structure of such types of implantable devices so as to secure hermeticity, that is to say, to prevent a body fluid or the like from contacting an electronic circuit and causing the electronic circuit to malfunction. For example, Patent Document 1 discloses a device for assisting visual restoration that includes a resin case having a depression for housing an electronic element and having an aperture on top, the electronic element incorporated into the case, a flexible wiring substrate connected to the electronic element, and a resin cap for sealing the electronic element and the flexible wiring substrate and that has a simplified casing structure. However, a casing larger than the casing-implanted body site causes such as bulging of the device-implanted site seen from outside the body. This is undesirable in terms of appearance. Further, a contact or friction with the bulging skin easily causes inflammation and in some cases may form a fistula, resulting in an infection. However, there has not been established any implantation technology that eliminates skin bulging caused by an implantable device and that is excellent in appearance.

SUMMARY OF THE INVENTION

Problems to be Solved by the Invention

Technology for simplifying the casing structure of an implantable device, such as the above-mentioned Patent Document 1, is useful in miniaturizing a device. However, there is a limit to miniaturizing an implantable device. Implanting an implantable device in a human body requires determining the implantation site while avoiding bones of a human body or body tissues. Accordingly, it must be said that the device implantation site is considerably limited. Depending on the body size, a device may be impossible to implant in the human body. For this reason, conventional implantable devices have often been implanted subcutaneously in the precordia or in the abdomen. This has caused a new problem, occurrence of noise by the elongation and enlargement of an analog cable connecting electrodes and the device. Specifically, for example, elongation of an analog cable connecting electrodes placed over the cerebral cortex and configured to obtain neural information, and an implantable device configured to receive neural signals measured by the electrodes would increase noise accordingly. As a result, information cannot be obtained accurately.

Such a problem can be resolved by implanting an implantable device in a head and reducing a distance dimension between the electrode and the implantable device and thus shortening the analog cable. However, implantation of a conventional implantable device in the head is problematic due to narrow layout space as described above, a skin elasticity problem under a head skin, or the like. Further, exposure of an implantable device to outside degrades an appearance of a patient, as well as may cause new problems such as the risk of an infection. Furthermore, implantation of a conventional implantable device in the body, including the head, easily causes skin bulging/depression or the like in the implantation site. Contact or friction with the bulging site may cause a complication such as a skin fistula.

An objective of the present invention is to solve the above-mentioned problems and allow an implantable device including an electronic circuit to be implanted in a human head more safely. Another objective of the present invention is to allow a casing of an implantable device to be supplied at a lower cost.

Means for Solving the Problems

Inventors, Hirata et al, have been involved in neurosurgeries as neurosurgeons, as well as in the development of implantable devices using brain-machine interfaces for the restoration of neurological function. In their capacities, the inventors have conceived an idea that, if an artificial bone designed in accordance with the shape of a skull resected from the craniotomy site of each patient is also used as a casing of an implantable device, the implantable device can be implanted in a human body more safely, reliably and cosmetically compared to conventional implantable devices such as Patent Document 1. Based on this idea, the inventors have completed the present invention. The inventors have also found that the technical concept that the artificial bone as described above is used as a casing of an implantable device can be applied to a skull, as well as to any bone if the bone is a relatively large bone such as long bones including the humerus and the femur, the pelvis, and the breast bone. Based on this finding, the inventors have completed the present invention.

Specifically, the present invention is a casing 16 of an implantable device 4 configured to be implanted in a human body. The casing 16 is characterized in that it includes an outer convexity surface 30 matching an external shape of a resected skull 27 related to at least a defect 26 of an artificial bone 28 designed in accordance with a bone shape of each person in order to fill the defect 26. Specific examples of a "bone" to which the implantable device 4 according to the present invention is applicable include long bones such as the femur and the humerus, the pelvis, and the breast bone. A "convexity" as used herein refers to a convexly curved shape. Needless to say, in the present invention, the shape of the artificial bone matching the external shape of the resected bone related to the defect is not limited to a circle in a plan view and may be a rectangle or the like.

The present invention is a casing 16 of an implantable device 4 configured to be implanted in a human head. The casing 16 is characterized in that it includes an outer convexity surface 30 matching an external shape of a resected skull 27 related to at least a craniotomy site 26 of an artificial bone 28 designed in accordance with a skull shape of each person in order to fill the craniotomy site 26.

Examples of a material for the artificial bone 28 serving as the casing 16 include metals, ceramic, and synthetic resins including FRP. The artificial bone 28 made of titanium or a titanium alloy is particularly optimum in terms of strength, processibility, biocompatibility, and the like.

A configuration may be used where the artificial bone 28 includes an outer convexity surface 30 matching an external shape of the resected skull 27 related to the craniotomy site 26, an inner convexity surface 31 matching an internal shape of the resected skull 27, and internal space 32 formed between the outer convexity surface 30 and the inner convexity surface 31, where the casing 16 includes the outer convexity surface 30 and the inner convexity surface 31, and where an electronic circuit 15 included in the implantable device 4 is fixed to the internal space 32.

A configuration may be used where a fixing boss 42 for fixing the electronic circuit 15 using a screw is formed on one of the outer convexity surface 30 and the inner convexity surface 31 in a manner protruding toward an inside of the artificial bone 28.

The present invention is also a casing 16 of an implantable device 4 configured to be implanted in a human body. The casing 16 is characterized in that it matches an external shape of a resected skull 27 related to at least a defect 26 of an artificial bone 28 designed in accordance with a bone shape of each person in order to fill the defect 26 and includes a block-shaped convexity 60 having a housing depression 61 for housing an electronic circuit 15 included in the implantable device 4.

The casing 16 may match an external shape of a resected skull 27 related to at least a craniotomy site 26 of the artificial bone 28 designed in accordance with a skull shape of each person in order to fill the craniotomy site 26 and include a block-shaped convexity 60 having a housing depression 61 for housing an electronic circuit 15 included in the implantable device 4.

The artificial bone 28 may include the convexity 60 and a cover plate 70 welded and fixed to an aperture of the housing depression 61 in a manner blocking the aperture.

The present invention is also directed to an implantable device 4 connected to a function unit 2 implanted in a human head via a cable 3 and configured to receive measured signals measured by the function unit 2 and/or control the function unit 2. The implantable device 4 includes an electronic circuit 15 and a casing 16 enclosing the electronic circuit 15. The implantable device 4 is characterized in that the casing 16 includes an outer convexity surface 30 matching an external shape of a resected skull 27 related to at least a craniotomy site 26 of an artificial bone 28 designed in accordance with a skull shape of each person in order to fill the craniotomy site 26. Specific examples of the "function unit" include electrodes for neural recording and electrodes for neural stimulation, as well as drug delivery systems and photosensors.

A configuration is preferably used where the artificial bone 28 includes an outer convexity surface 30 matching an external shape of the resected skull 27 related to the craniotomy site 26, an inner convexity surface 31 matching an internal shape of the resected skull 27, and internal space 32 formed between the outer convexity surface 30 and the inner convexity surface 31, where the casing 16 includes the outer convexity surface 30 and the inner convexity surface 31, and where an electronic circuit 15 included in the implantable device 4 is fixed to the internal space 32.

A configuration may be used where a hole 24 for a screw 23 is formed on a circuit board 18 included in the electronic circuit 15 and where a fixing boss 42 for fixing the circuit board 18 using a screw is formed on one of the outer convexity surface 30 and the inner convexity surface 31 in a manner protruding toward an inside of the artificial bone 28.

A configuration is preferably used where the electronic circuit 15 includes two or more circuit boards 18 and a flexible printed wiring 19 electrically connecting the circuit boards 18 and where the electronic circuit 15 is configured to be bendable around a connection made by the flexible printed wiring 19. A configuration is preferably used where a through hole 24 for a screw 23 is formed on each of the two or more circuit boards 18 and where each circuit board 18 is fixed to the fixing boss 42 using a screw, the fixing boss 42 being formed on one of the outer convexity surface 30 and the inner convexity surface 31 in a protruding manner.

The present invention is also a implantable device 4 connected to a function unit 2 implanted in a human head via a cable 3 and configured to receive measured signals transmitted by the function unit 2 and/or control the function unit 2. The implantable device 4 includes an electronic circuit 15 and a casing 16 enclosing the electronic circuit 15. The casing 16 includes a block-shaped convexity 60 having a housing depression 61 into which the electronic circuit 15 is to be inserted and a flat cover plate 70 for blocking an aperture of the housing depression 61. The convexity 60 is a machined metal product having an external surface 601 matching an external shape of a resected skull 27 related to a craniotomy site 26, a side surface 602 matching a side surface shape of the resected skull 27, and an inner surface 603 matching an internal shape of the resected skull 27. A housing depression 61 is formed in the surface center of the inner surface 603 in a depressed manner. The cover plate 70 is made of a metal. The implantable device 4 is characterized in that the cover plate 70 to which the electronic circuit 15 is fixed is welded and fixed to a periphery of an aperture of the housing depression 61 of the convexity 60.

A depressed space 63 having a receiving surface 631 oriented toward the brain is formed between the inner surface 603 of the convexity 60 and an inner side surface 611 of the housing depression 61 in a depressed manner. The periphery of the cover plate 70 is welded and fixed to a side surface 632 of the depressed space 63. A configuration may be used where, in a state where the cover plate 70 is welded and fixed to the side surface 632 of the depressed space 63, the external surface of the cover plate 70 adjacent to the human head is located closer to the housing depression 61 than the inner surface 603 of the convexity 60.

A configuration is preferably used where the electronic circuit 15 includes two or more circuit boards 18 and a flexible printed wiring 19 electrically connecting the circuit boards 18 and where the electronic circuit 15 is configured to be bendable around a connection made by the flexible printed wiring 19.

The present invention is also directed to a method for manufacturing a casing 16 of an implantable device 4 configured to be implanted in a human head. The implantable device 4 uses, as the casing 16, an artificial bone 28 designed in accordance with a skull shape of each person in order to fill a craniotomy site 26. The method is characterized in that it includes: a craniotomy site determination step of determining the craniotomy site 26 on the basis of head CT data; an artificial bone design step of designing the artificial bone 28 using a computer-aided design system (CAD) on the basis of the head CT data, the artificial bone 28 having an outer convexity surface 30 matching an external shape of a resected skull 27 related to the craniotomy site 26 of each person, an inner convexity surface 31 matching an internal shape of the resected skull 27, and internal space 32 formed between the outer convexity surface 30 and the outer convexity surface 31, the artificial bone 28 being configured to fill the craniotomy site 26; an electronic circuit layout check step of checking using CAD whether the electronic circuit 15 included in the implantable device 4 can be laid out within the internal space 32 of the artificial bone 28; a design change step of, if it is determined in the electronic circuit layout check step that the electronic circuit 15 cannot be laid out within the internal space 32, returning the craniotomy site determination step and the artificial bone design step; and a step of, when it is determined in the electronic circuit layout check step that the electronic circuit 15 can be laid out within the internal space 32, manufacturing the artificial bone 28 using CAM or 3D printing such as selective laser melting or direct metal laser sintering on the basis of CAD data having a shape designed in the artificial bone design step.

If it is determined in the electronic circuit layout check step that the electronic circuit 15 cannot be laid out within the internal space 32, the process may return to the artificial bone design step to make a design change to swell out the outer convexity surface 30 outwardly by an amount required to lay out the electronic circuit 15 so that the electronic circuit 15 can be laid out within the internal space 32.

The present invention is also a method for manufacturing a casing 16 of an implantable device 4 configured to be implanted in a human head. The implantable device 4 uses, as the casing 16, an artificial bone 28 designed in accordance with the skull shape of each person in order to fill a craniotomy site 26. The artificial bone 28 has an external surface 601 matching an external shape of a resected skull 27 related to the craniotomy site 26 of each person, a side surface 602 matching a side surface shape of the resected skull 27, and an inner surface 603 matching an internal shape of the resected skull 27. The artificial bone 28 includes, in the surface center of the inner surface 603, a convexity 60 where a housing depression 61 into which the electronic circuit 15 included in the implantable device 4 is to be inserted is formed in a depressed manner and a flat cover plate 70 welded and fixed in a manner blocking the aperture 62 of the housing depression 61, the cover plate 70 being a cover plate where the electronic circuit 15 is fixed to a wall surface oriented toward the housing depression 61. The method for manufacturing a casing 16 according to the present invention includes: a craniotomy site determination step of determining the craniotomy site 26 on the basis of head CT data; an artificial bone design step of designing an external shape of a convexity 60 using CAD on the basis of the head CT data, the convexity 60 being included in the artificial bone 28 for filling the craniotomy site 26; an electronic circuit layout position determination step of determining the layout position of the electronic circuit 15 in the convexity 60; a cover layout position determination step of determining the layout position of the cover plate 70 in accordance with the layout position of the electronic circuit 15; a housing depression layout position determination step of determining the layout position of the housing depression 61 on the basis of the layout positions of the electronic circuit 15 and the cover plate 70 determined in the electronic circuit layout position determination step and the cover layout position determination step; a layout check step of checking using CAD whether a thickness dimension of the convexity 60 in the housing depression 61 is a predetermined thickness dimension; a design change step of, if it is determined in the layout check step that the thickness dimension of the convexity 60 in the housing depression 61 is not the predetermined thickness dimension, returning to the electronic circuit layout position determination step to change the design of the layout position of the electronic circuit 15; and a step of, if it is determined in the layout check step that the thickness dimension of the convexity 60 in the housing depression 61 is the predetermined thickness dimension, manufacturing the artificial bone 28 including the convexity 60 and the cover plate 70 using CAM or 3D printing such as selective laser melting or direct metal laser sintering on the basis of CAD data having a designed shape.

A depressed space 63 having a receiving surface 631 oriented toward the brain is formed at a corner between an inner surface 603 of the convexity 60 and a side surface 611 of the housing depression 61. An edge of the cover plate 70 is welded and fixed to the side surface 632 of the depressed space 63 with the edge received by the receiving surface 631. The method for manufacturing a casing according to the present invention further includes a depressed space layout position determination step of determining the layout position of the depressed space 63, the depressed space layout position determination step following the housing depression layout position determination step. The layout check step includes checking using CAD whether the thickness dimension of the convexity 60 in the housing depression 61 is a predetermined thickness dimension, as well as whether a predetermined height dimension is secured between the periphery of the cover plate 70 and the inner surface 603 of the convexity 60.

The present invention is also a method for supporting treatment of neuromuscular diseases by assisting movement, communication, visual function or hearing function using an implantable device 4. The implantable device 4 is connected to a function unit 2 via a cable 3, the function unit 2 being configured to measure an electric signals passing through the brain or nerve and/or electrically stimulate the brain or nerve. The implantable device 4 is configured to receive measured signals measured by the function unit 2 and/or control the function unit 2. The method is characterized in that a casing 16 of the implantable device 4 matches an external shape of a resected skull 27 related to at least a defect 26 of an artificial bone 28 designed in accordance with a bone shape of each person in order to fill the defect 26 and includes a block-shaped convexity 60 having a housing depression 61 for housing an electronic circuit 15 included in the implantable device 4.

The casing 16 matches an external shape of a resected skull 27 related to at least a craniotomy site 26 of the artificial bone 28 designed in accordance with a skull shape of each person in order to fill the craniotomy site 26 and includes a block-shaped convexity 60 having a housing depression 61 for housing an electronic circuit 15 included in the implantable device 4.

The artificial bone 28 includes the convexity 60 and a cover plate 70 welded and fixed to an aperture of the housing depression 61 in a manner blocking the aperture.

Advantages of the Invention

In the present invention, the outer convexity surface 30 matching the external shape of the resected skull 27 related to at least the craniotomy site 26 of the artificial bone 28 designed in accordance with the shape of the skull 29 of each person in order to fill the craniotomy site 26 is used as the casing of the implantable device 4. That is, the outer convexity surface 30 of the artificial bone 28 is provided with two functions: the original function of filling the craniotomy site 26 as the artificial bone 28 and a function of serving as the casing 16 of the implantable device 4.

This type of artificial bone 28 is originally intended to fill the craniotomy site 26. In particular, the outer convexity surface 30 made of a metal has sufficient strength to withstand an external shock or the like, as with the skull. Thus, according to the present invention, the casing 16 of the implantable device 4 that has sufficient strength to withstand an external shock or the like and that is excellent in safety and reliability can be obtained. This means that the implantable device 4 can be safely implanted in the head, helping increase the reliability of the implantable device 4.

Further, using, as the casing 16 of the implantable device 4, the outer convexity surface 30 of the artificial bone 28 matching the external shape of the resected skull 27 related to the craniotomy site 26 eliminates the possibility that the implantable device 4 implanted in the head may appear on the outer surface of the head. Further, since the outer convexity surface 30 of the artificial bone 28 matches the external shape of the resected skull 27 related to the craniotomy site 26, the craniotomy site 26 can be filled with the outer convexity surface 30 (casing 16) matching the shape of the skull 29 of each patient. Thus, the implantable device 4 can be implanted in the head without bulging of the skin by the implantable device and without causing an uncomfortable feeling in terms of appearance. As seen, according to the present invention, the casing 16 of the implantable device 4 that resolves the patient's appearance impairment problem and that is excellent in practical utility can be provided. Further, the occurrence risk of complications such as a skin fistula caused by contact or friction with the bulging skin site can be reduced.

A configuration may be used where the artificial bone 28 includes the outer convexity surface 30 matching the external shape of the resected skull 27 related to the craniotomy site 26, the inner convexity surface 31 matching the internal shape of the resected skull 27, and internal space 32 formed between the outer convexity surface 30 and the inner convexity surface 31, where the casing 16 includes the outer convexity surface 31 and the inner convexity surface 30, and where an electronic circuit 15 included in the implantable device 4 is fixed to the internal space 32. That is, a configuration may be used where the outer convexity surface 30 of the artificial bone 28, as well as the inner convexity surface 31 thereof are used as the casing 16 of the implantable device 4.

Thus, the entire electronic circuit 15 can be placed within the artificial bone 28 having excellent strength, obtaining the implantable device 4 having excellent shock resistance. There is also an advantage of eliminating the possibility that such as unexpected displacement of the electronic circuit 15 may occur and increasing the reliability of the implantable device 4. Among others, the shape of the inner convexity surface 31 included in the casing 16 matches the internal shape of the resected skull 27 related to the craniotomy site 26. Thus, the bulging site of the inner convexity surface 31 is prevented from compressing the brain. This eliminates the possibility that neurological deficits such as paralyses of the extremities may be caused by cerebral compression. As a result, the implantable device 4 that is excellent in safety can be provided.

A configuration may be used where the fixing boss 42 for fixing the electronic circuit 15 using a screw is formed on one of the outer convexity surface 30 and the inner convexity surface 31 in a manner protruding toward the inside of the artificial bone 28. Thus, the electronic circuit 15 can surely be fixed and fixed using the screws 23. As a result, the implantable device 4 that is excellent in long-term reliability compared to a configuration where the electronic circuit 15 is bonded and fixed to the inner surface of the outer convexity surface 30 or the inner convexity surface 31 can be obtained. Further, the fixing boss 42 is formed in a manner protruding toward the inside of the artificial bone 28. This can prevent the screw 23 from protruding from the casing and does not degrade the appearance of the patient.

In particular, the outer convexity surface 30 and the inner convexity surface 31 are designed in accordance with the skull shape of each person. For this reason, the internal space 32 formed between these surfaces also depends on the skull shape of each person and is spatially limited. Accordingly, in the configuration where the relatively large electronic circuit 15 is placed within the limited internal space 32, how the layout space of the electronic circuit 15 is rationally secured is important. Specifically, since the entire artificial bone 28 matching the shape of the resected skull 27 is curved in the shape of a spherical shell, the size of the electronic circuit 15 that can be laid out within the internal space 32 is limited. In particular, where a single flat circuit board is placed within the artificial bone 28 (casing 16), the size is limited. For this reason, if the electronic circuit 15 includes two or more circuit boards 18 and the flexible printed wiring 19 electrically connecting the circuit boards 18 and the electronic circuit 15 is configured to be bendable around the connection made by the flexible printed wiring 19, as in the present invention, the electronic circuit 15 can be placed within the narrow internal space 32 more easily and surely by laying out the integrated circuit boards 18 along the curved internal space 32. This means that the artificial bone 28 (casing 16) can be prevented from being upsized unnecessarily due to the placement of the electronic circuit 15, that is, the craniotomy site 26 can be prevented from being upsized unnecessarily. This contributes to less invasiveness to the patient. Since the artificial bone 28 (casing 16) can be miniaturized, the cost of the material for the artificial bone 28 can be reduced, contributing to a reduction in the manufacturing cost of the artificial bone 28 (casing 16). Further, since the design flexibility of the artificial bone 28 (casing 16) is considerably increased, the casing 16 and the implantable device 4 that are excellent in versatility can be advantageously provided.

A configuration may be used where a hole 24 for a screw 23 is formed on each of the two or more circuit boards 18 and where the fixing boss 42 for fixing the circuit board 18 using a screw is formed on one of the outer convexity surface 30 and the inner convexity surface 31 in a manner protruding toward the inside of the artificial bone 28. Thus, the implantable device 4 that surely prevents unexpected displacement of the separated circuit boards 18 and is excellent in reliability can be obtained.

Further, in the present invention, the block-shaped convexity 60 that matches the external shape of the resected skull 27 related to at least the craniotomy site 26 of the artificial bone 28 designed in accordance with the shape of the skull 29 of each person in order to fill the craniotomy site 26 and that has the housing depression 61 for housing the electronic circuit 15 included in the implantable device 4 is used as the casing of the implantable device 4. That is, the convexity 60 of the artificial bone 28 is provided with two functions: the original function of filling the craniotomy site 26 as the artificial bone 28 and a function of serving as the casing 16 of the implantable device 4.

This type of artificial bone 28 is originally intended to fill the craniotomy site 26. In particular, the convexity 60 made of a metal has sufficient strength to withstand an external shock or the like, as with the skull. Thus, according to the present invention, the casing 16 of the implantable device 4 that has sufficient strength to withstand an external shock or the like and is excellent in safety and reliability can be obtained. This means that the implantable device 4 can safely be implanted in the head, helping increase the reliability of the implantable device 4.

Further, since the convexity 60 of the artificial bone 28 matching the external shape of the resected skull 27 related to the craniotomy site 26 is used as the casing 16 of the implantable device 4, there is no possibility that the implantable device 4 implanted in the head may appear on the external surface of the head. Further, since the convexity 60 of the artificial bone 28 matches the external shape of the resected skull 27 related to the craniotomy site 26, the craniotomy site 26 can be filled with the convexity 60 matching the shape of the skull 29 of each person. Thus, the implantable device 4 can be implanted in the head without causing bulging of a skin by the implantable device and is preferable from a cosmetic point of view. As seen, according to the present invention, the casing 16 of the implantable device 4 that resolves the patient's cosmetic problem and is excellent in practical utility can be provided. Further, the occurrence risk of complications such as a skin fistula caused by contact or friction with the bulging skin site can be reduced.

Further, since the casing 16 is composed of the block-shaped convexity 60, much larger rigidity can be given to the casing 16 compared to a casing having a shape of a bottomed container and composed of the outer convexity surface 30 and the inner convexity surface 31. Thus, the casing 16 that is excellent in shock resistance or the like can be obtained.

The casing 16 may include the block-shaped convexity 60 having the housing depression 61 into which the electronic circuit 15 is to be inserted and the flat cover plate 70 welded and fixed to the periphery of an aperture of the housing depression 61 in a manner blocking the aperture of the housing depression 61. Thus, the entire electronic circuit 15 can be placed within the artificial bone 28 (casing 16) having excellent strength, obtaining the implantable device 4 having excellent shock resistance. There is also an advantage of eliminating the possibility that such as unexpected displacement of the electronic circuit 15 may occur and increasing the reliability of the implantable device 4. Among others, since the shape of the inner surface 603 included in the casing 16 matches the internal shape of the resected skull 27 related to the craniotomy site 26, the bulging site of the inner surface 603 does not compress the brain. This eliminates the possibility that neurological deficits such as the paralysis of the extremities may be caused by brain compression. As a result, the implantable device 4 that is excellent in safety can be provided.

A configuration may be used where the depressed space 63 having the receiving surface 631 oriented toward a brain is formed between the inner surface 603 of the convexity 60 and the inner side surface 611 of the housing depression 601 in a depressed manner, where the periphery of the cover plate 70 is welded and fixed to the side surface 632 of the depressed space 63, and where the external surface of the cover plate 70 adjacent to a human head is located closer to the housing depression 601 than the inner surface 603 of the convexity 60 with the cover plate 70 welded and fixed to the side surface 632 of the depressed space 63. Thus, a weld bead 71 formed in the weld portion of the cover plate 70 can surely be prevented from protruding from the inner surface 603 of the convexity 60 toward the brain. That is, the bulging weld bead 71 can surely be prevented from protruding from the inner surface 603 of the convexity 60 toward the brain. Thus, the bulging site of the inner surface of the artificial bone 28 (casing 16) including the weld bead 71 can be prevented from compressing the brain. This eliminates the possibility that neurological deficits such as paralyses of the extremities may be caused by cerebral compression. As a result, the implantable device 4 that is excellent in safety can be provided.

According to the method for manufacturing a casing of an implantable device according to the present invention, the processing technique using CAD/CAM or a 3D printer is used. Thus, the artificial bone 28 (casing 16) matching the shape of the skull 29 of each patient can be manufactured with high shape accuracy and high dimension accuracy. Further, the artificial bone 28 (casing 16) matching the shape of the skull 29 of each patient can be provided at relatively low cost and with ease.

Specifically, in this type of neurosurgery, the craniotomy site 26 varies depending on the case, and the shape of the resected skull 27 related to the craniotomy site 26 varies from person to person. Accordingly, the shape of the artificial bone 28 varies from patient to patient. Further, in a configuration where the artificial bone 28 is used as the casing 16 and where the electronic circuit 15 is placed within the artificial bone 28, as in the present invention, the shape of the artificial bone 28 is determined simply in accordance with the shape of the resected skull 27 at the craniotomy site 26. Further, the artificial bone 28 must be designed in such a manner that the electronic circuit 15 can be placed within the artificial bone 28. By using the processing technique using CAD/CAM or a 3D printer as in the present invention and designing the artificial bone 28 (casing 16) using CAD before a craniotomy from a viewpoint of whether the artificial bone 28 matches the shape of the resected skull 27 at the craniotomy site 26, as well as from a viewpoint of whether the electronic circuit 15 can be placed within the artificial bone 28 and, in some cases, changing the design, including the determination of the craniotomy site 26, the casing 16 of the implantable device 4 that is excellent in shape accuracy and dimension accuracy, that completely matches the shape of the skull 29 of each patient, and that is configured in such a manner that the electronic circuit 15 can be placed within the narrow internal space 32 can be manufactured rapidly at low cost.

If it is determined in the electronic circuit layout check step that the electronic circuit 15 cannot be laid out within the internal space 32, the process preferably returns to the artificial bone design step to make a design change to swell out the outer convexity surface 30 outwardly so that the electronic circuit 15 can be laid out within the internal space 32. As seen, making a design change to swell out the outer convexity surface 30 outwardly reduces the possibility that the brain tissue (dura, etc.) may be compressed, compared to a configuration where the inner convexity surface 31 swells out. Thus, the casing 16 (artificial bone 28) that is more excellent in safety can be obtained. Needless to say, such a design change is made when it is difficult to change the craniotomy site or increase the external dimension of the artificial bone 28, and the bulging dimension should be minimized so as not to impair the appearance when the artificial bone 28 is inserted.

If the artificial bone 28 includes the block-shaped convexity 60, the layout check step of determining whether the thickness dimension of the convexity 60 in the housing depression 61 is larger than the predetermined thickness dimension is included. If it is determined in the layout check step that the thickness dimension of the convexity 60 in the housing depression 61 is less than the predetermined thickness dimension, the process returns to the electronic circuit layout position determination step to change the design of the layout position of the electronic circuit. This is because if the thickness dimension of the convexity 60 in the housing depression 61 is small, shock resistance is reduced. This is also because if the thickness dimension of the convexity 60 in the housing depression 61 is small, it is difficult to machine the convexity 60.

In a configuration where the edge of the cover plate 70 is welded and fixed to the side surface 632 of the depressed space 63 with the edge received by the side surface 632 of the depressed space 63, it is preferably checked using CAD in the layout check step whether a predetermined height dimension between the periphery of the cover plate 70 and the inner surface 603 of the convexity 60 is secured. Checking in the layout check step that the predetermined height dimension is secured between the periphery of the cover plate 70 and the inner surface 603 of the convexity 60 is intended to surely prevent the weld bead 71 formed between the cover plate 70 and the side surface 632 of the depressed space 63 of the cover plate 70 from protruding from the inner surface 603 of the convexity 60 toward the brain. Thus, the weld bead 71 formed in the weld portion of the cover plate 70 can surely be prevented from protruding from the inner surface 603 of the convexity 60 toward the brain. That is, the bulging weld bead 71 can surely be prevented from protruding from the inner surface 603 of the convexity 60 toward the brain. Thus, the bulging site of the inner surface of the artificial bone 28 (casing 16) including the weld bead 71 can be prevented from compressing the brain. This eliminates the possibility that neurological deficits may be caused by cerebral compression such as paralysis of the extremities. As a result, the implantable device 4 that is excellent in safety can be provided.

BRIEF DESCRIPTION OF THE DRAWINGS

FIG. 4 is an exploded view of the implantable device.

DETAILED DESCRIPTION

First Embodiment

Figure 1:
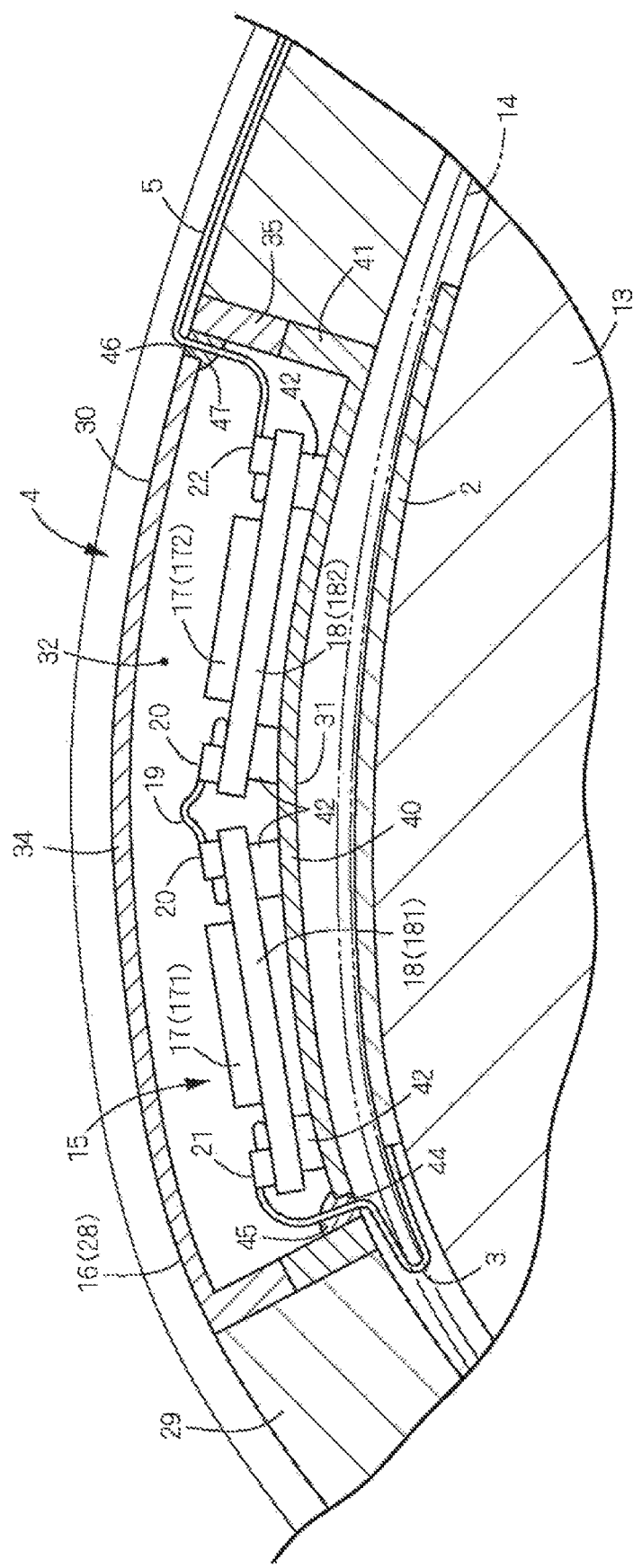
FIG. 1 is a longitudinal sectional front view showing main portions of an implantable device and a casing according to a first embodiment of the present invention.
Figure 2:
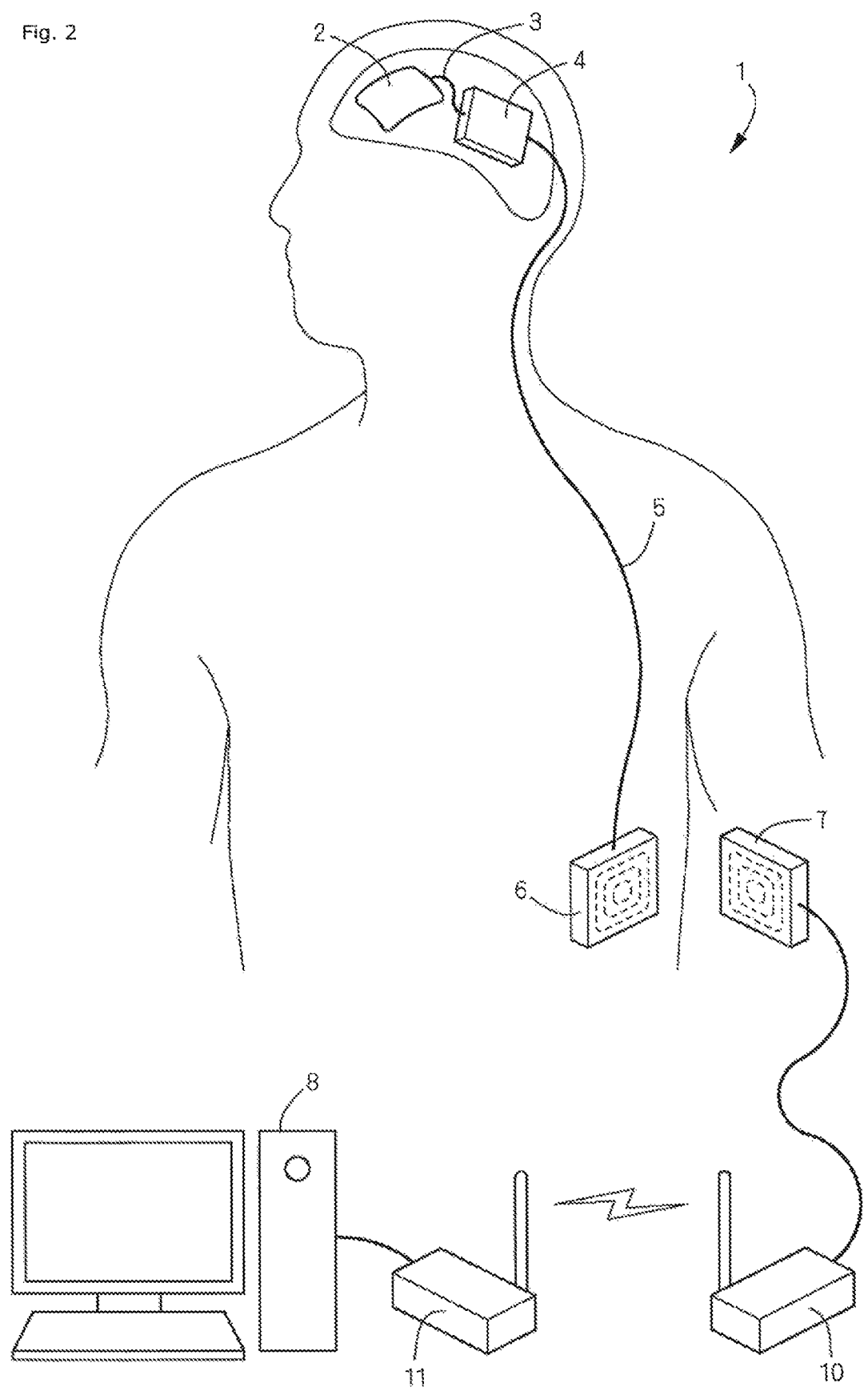
FIG. 2 is a drawing showing a head signal measurement system to which the implantable device is applied.
Figure 3:
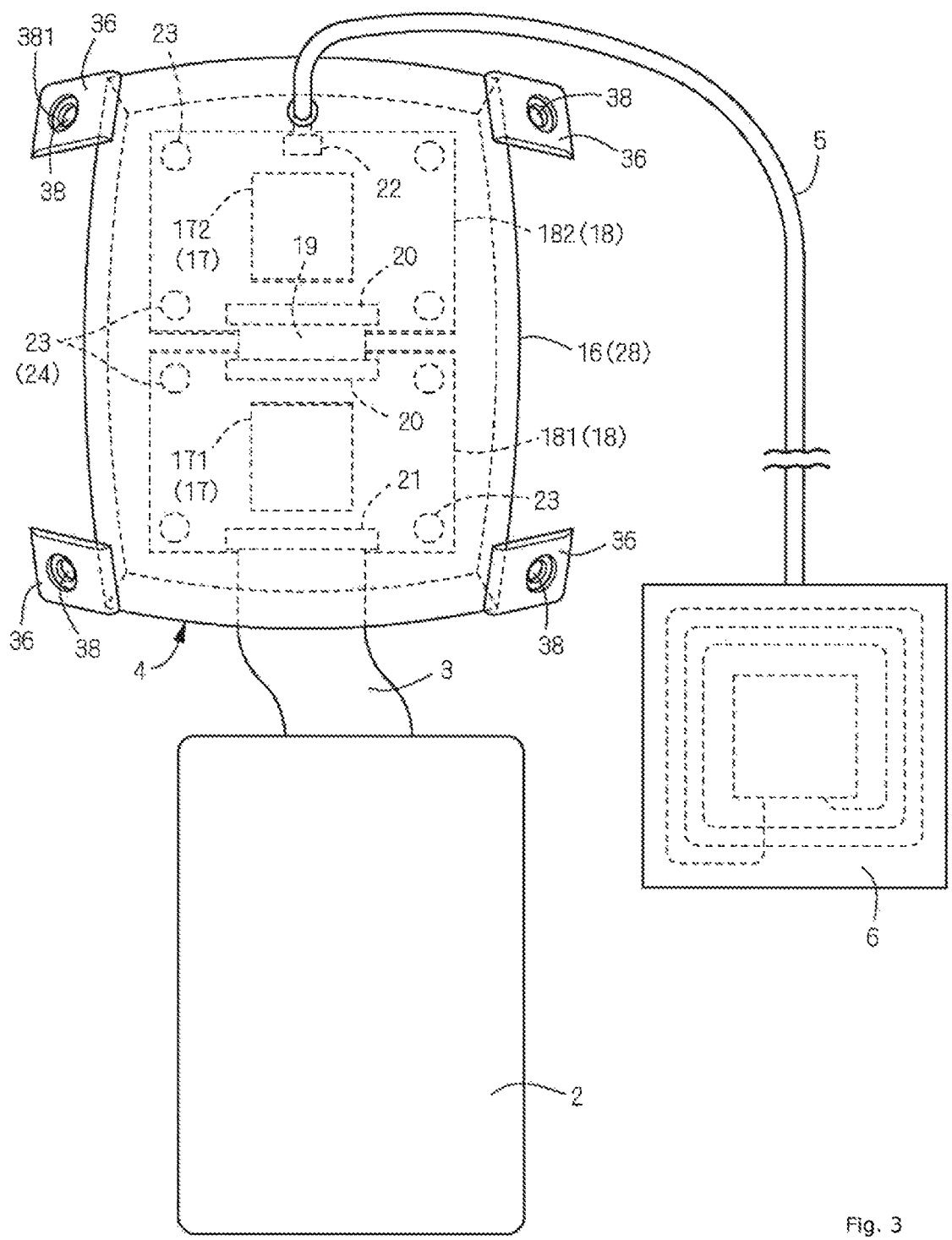
FIG. 3 is plan views of the implantable device, a sheet-shaped grid electrode array, and an internal transceiver.
Figure 5:
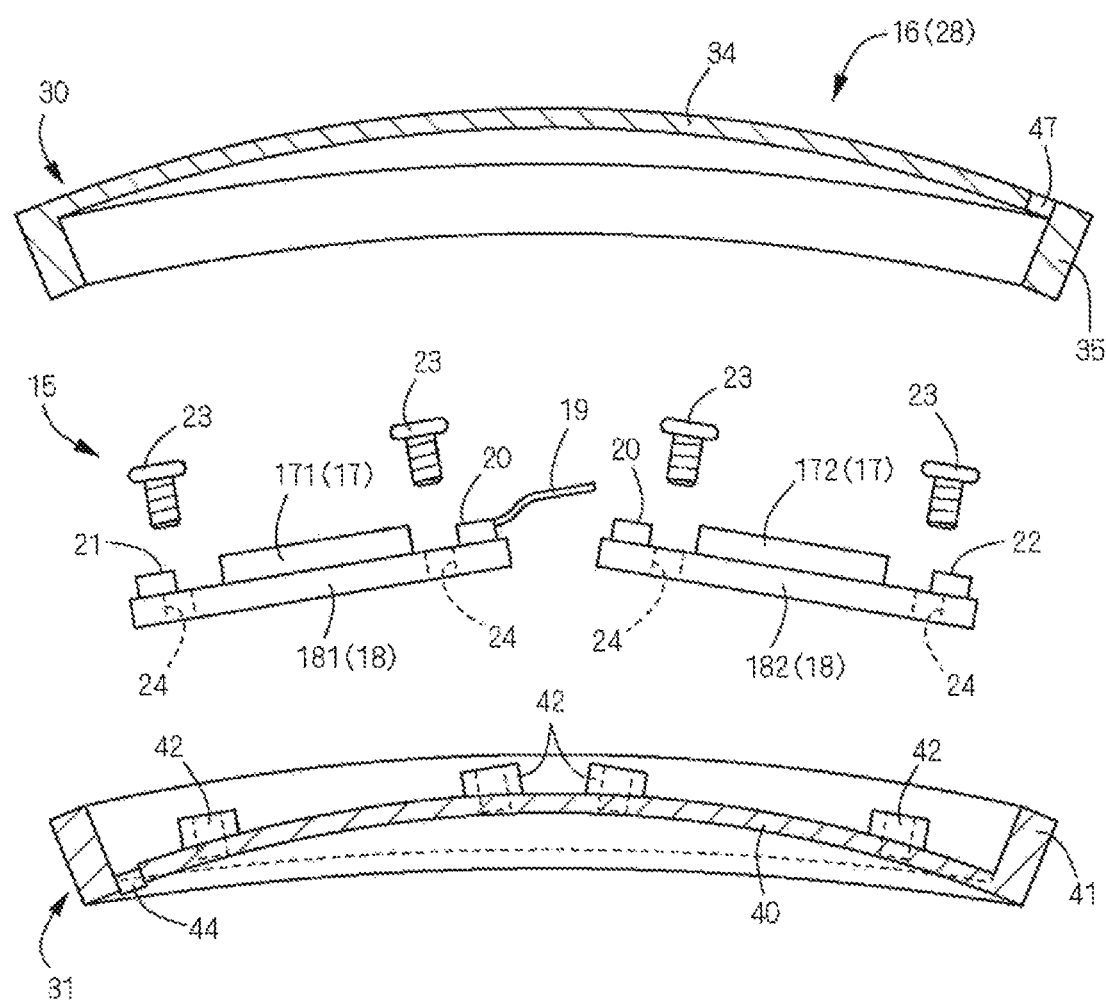
FIG. 5 is an exploded view of the implantable device.

FIGS. 1 to 10 show an embodiment where an implantable device according to the present invention is applied to a brain signal measurement system. As shown in FIGS. 1 and 2, the brain signal measurement system 1 is a system for measuring electrocorticograms. It includes a sheet-shaped grid electrode array (function unit) 2 for brain signal (electrocorticogram) measurement, an implantable device 4 connected to the sheet-shaped grid electrode array 2 via an analog cable (cable) 3, an internal transceiver 6 connected to the implantable device 4 via a digital cable 5 and configured to be implanted subcutaneously in the abdomen, an external transceiver 7 wirelessly connected to the internal transceiver 6, and a personal computer (hereafter simply referred to as "computer") 8 for neural signal processing. Signs 10, 11 represent wireless transceivers 10, 11 laid out between the external transceiver 7 and the computer 8 and forming a wireless LAN. The computer 8 receives a measurement result from the external transceiver 7 via the wireless transceivers 10, 11 and displays it on a display screen. Alternatively, the wireless transceiver 11 may be configured to be capable of receiving a signal transmitted by the internal transceiver 6. Needless to say, if a wired LAN is constructed, the wireless transceivers 10, 11 can be abandoned.

The sheet-shaped grid electrode array 2 is disposed under the dural membrane. In this embodiment, it is fixed to the surface of a brain 13 (the surface of the brain cortex), such as the cerebral cortex (See FIG. 1). The sheet-shaped grid electrode array 2 is a high-density electrode in which many electrodes are disposed with high density, and measures electrocorticograms in many points on the surface of the brain 13. Electrocorticographic signals measured by the sheet-shaped grid electrode array 2 is transmitted to the implantable device 4 via the analog cable 3 while remaining an analog signal. Examples of the analog cable 3 include a 128-wire cable.

The implantable device 4 is fixed adjacent to the sheet-shaped grid electrode array 2. In this embodiment, it is fixed above the sheet-shaped grid electrode array 2 in the brain. The implantable device 4 amplifies and digitizes measured signals (analog signals) transmitted by the sheet-shaped grid electrode array 2 via the analog cable 3. It includes an electronic circuit 15 and a casing 16 enclosing the electronic circuit 15. The electronic circuit 15 includes IC chips 17 and circuit boards 18 having the IC chips 17 mounted thereon. Each IC chip 17 performs such as a process of amplifying the analog signals (measured signals) transmitted by the sheet-shaped grid electrode array 2 and converting the analog signals into digital signals and a process of transmitting the digital signals to the internal transceiver 6. The electronic circuit 15 according to this embodiment includes two rectangular circuit boards, 181 and 182, IC chips 171, 172 mounted on the rectangular circuit boards 181, 182, respectively, and a flexible printed wiring 19 electrically connecting the rectangular circuit boards 181, 182. It is configured to be bendable around the connection made by the flexible printed wiring 19. Mounted on the opposite sides of both circuit boards, 181 and 182, are connectors 20 for connecting with the flexible printed wiring 19. While the circuit board 181 has a connector 21 for connecting with the analog cable 3 mounted thereon, the circuit board 182 has a connector 22 for connecting with the digital cable 5 mounted thereon. Through holes 24 for screws 23 are made at the four corners of each of the circuit boards 181, 182.

Figure 8:
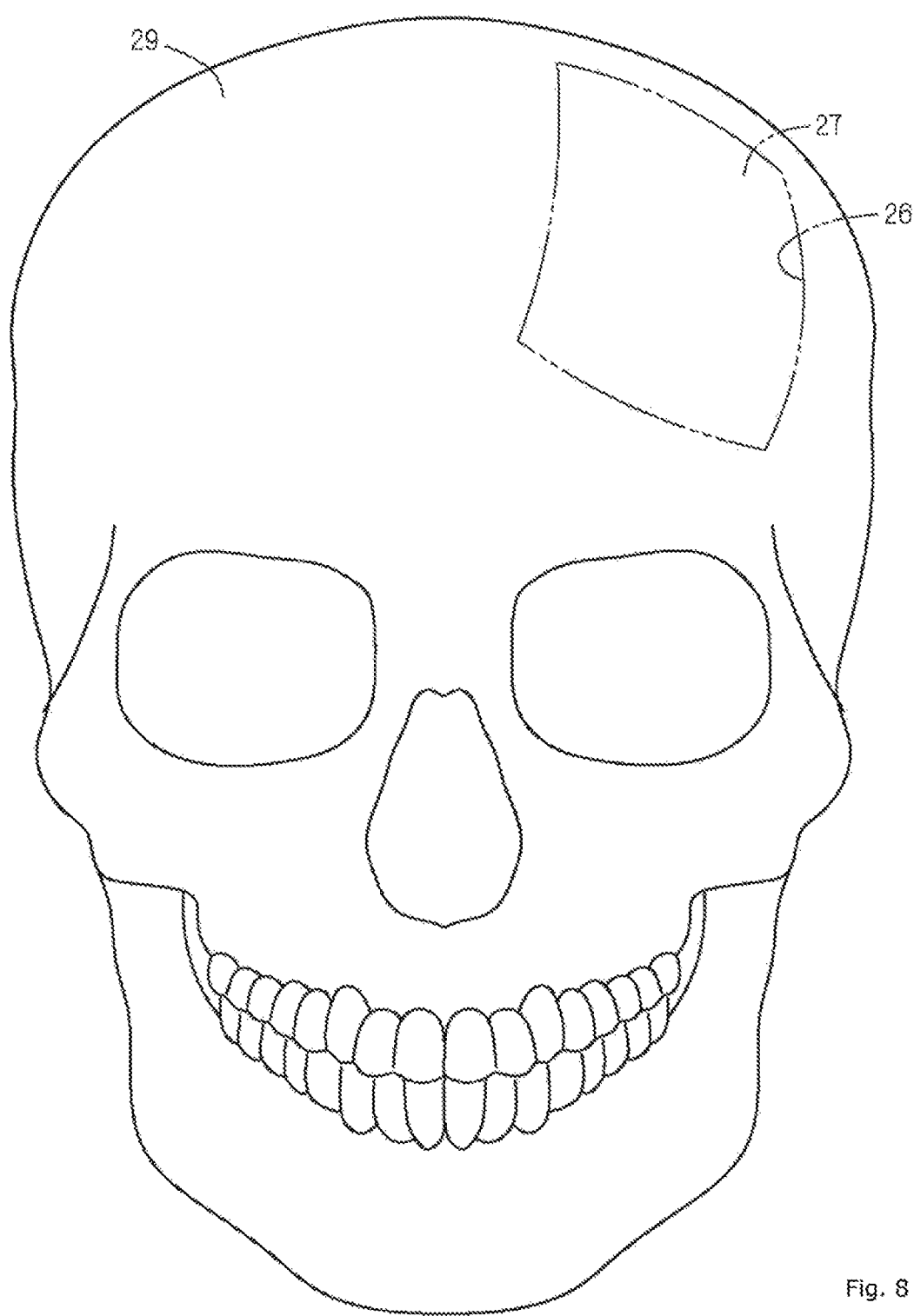
FIG. 8 is a drawing showing the position to which the implantable device is fixed (craniotomy site).
Figure 9:
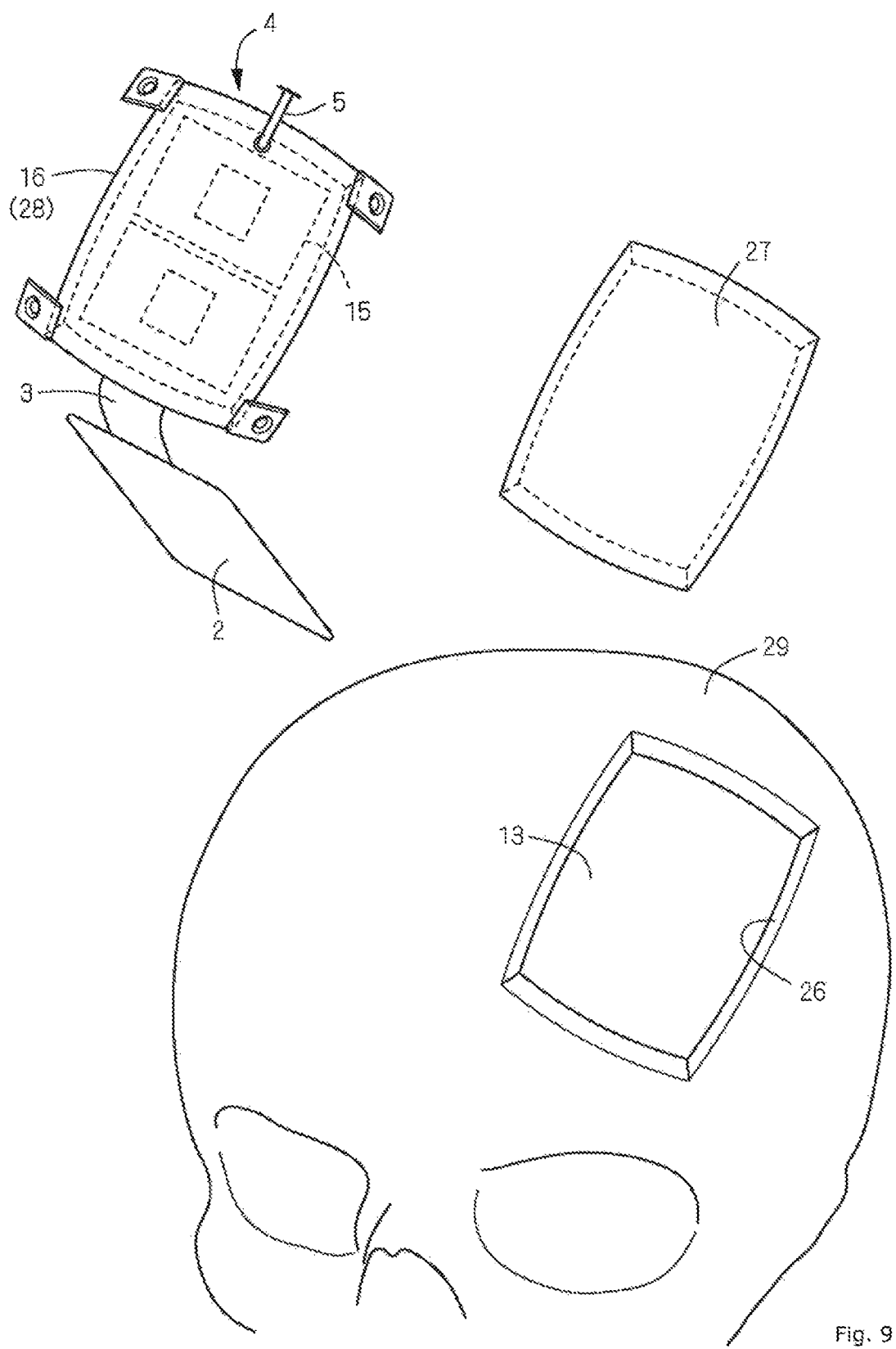
FIG. 9 is a drawing showing a method for fixing the implantable device to the skull (craniotomy site).
Figure 10:
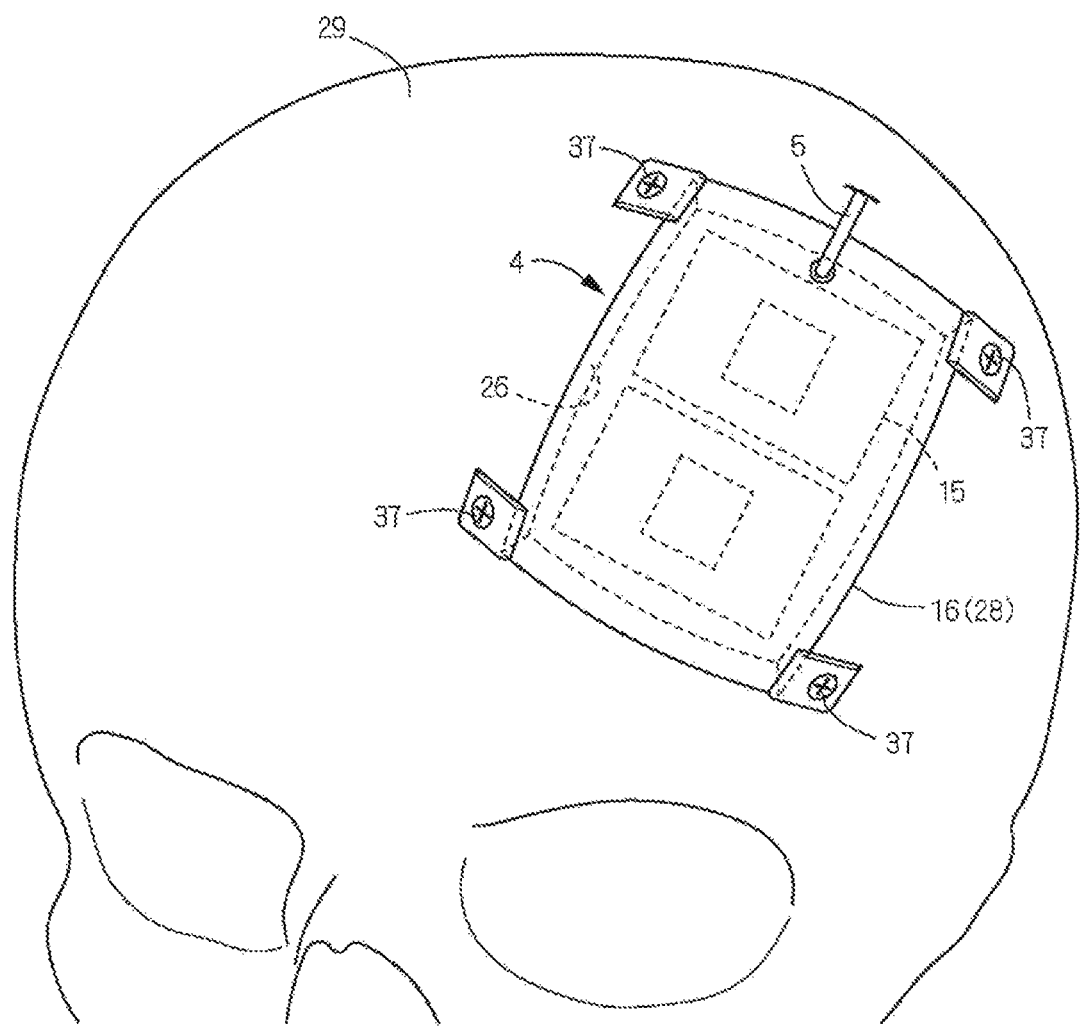
FIG. 10 is a drawing showing an aspect where the implantable device according to the present invention is placed in the skull.

As shown in FIGS. 8 to 10, the implantable device 4 uses, as the casing 16, an artificial bone 28 that has a shape matching a resected skull 27 at a craniotomy site (defect) 26 and that is implanted to fill the craniotomy site 26. That is, the implantable device 4 uses, as the casing 16, the artificial bone 28 placed within the craniotomy site 26 of a human skull 29 instead of the resected skull 27 after a neurosurgery.

As shown in FIGS. 1, 4, 5, 6, 7, the artificial bone 28 is formed by butt-welding and joining an outer convexity surface 30 and an inner convexity surface 31, which are a pair of separately formed inner and outer surfaces. Specifically, the artificial bone 28 includes the outer convexity surface 30 located above and having an external shape matching the external shape of the resected skull 27 related to the craniotomy site 26 and the inner convexity surface 31 located below and having an internal shape matching the internal shape of the resected skull 27. It is formed by butt-welding and joining both 30 and 31. The artificial bone 28 has internal space 32 for incorporating the electronic circuit 15 between the outer convexity surface 30 and the inner convexity surface 31.

Figure 6:
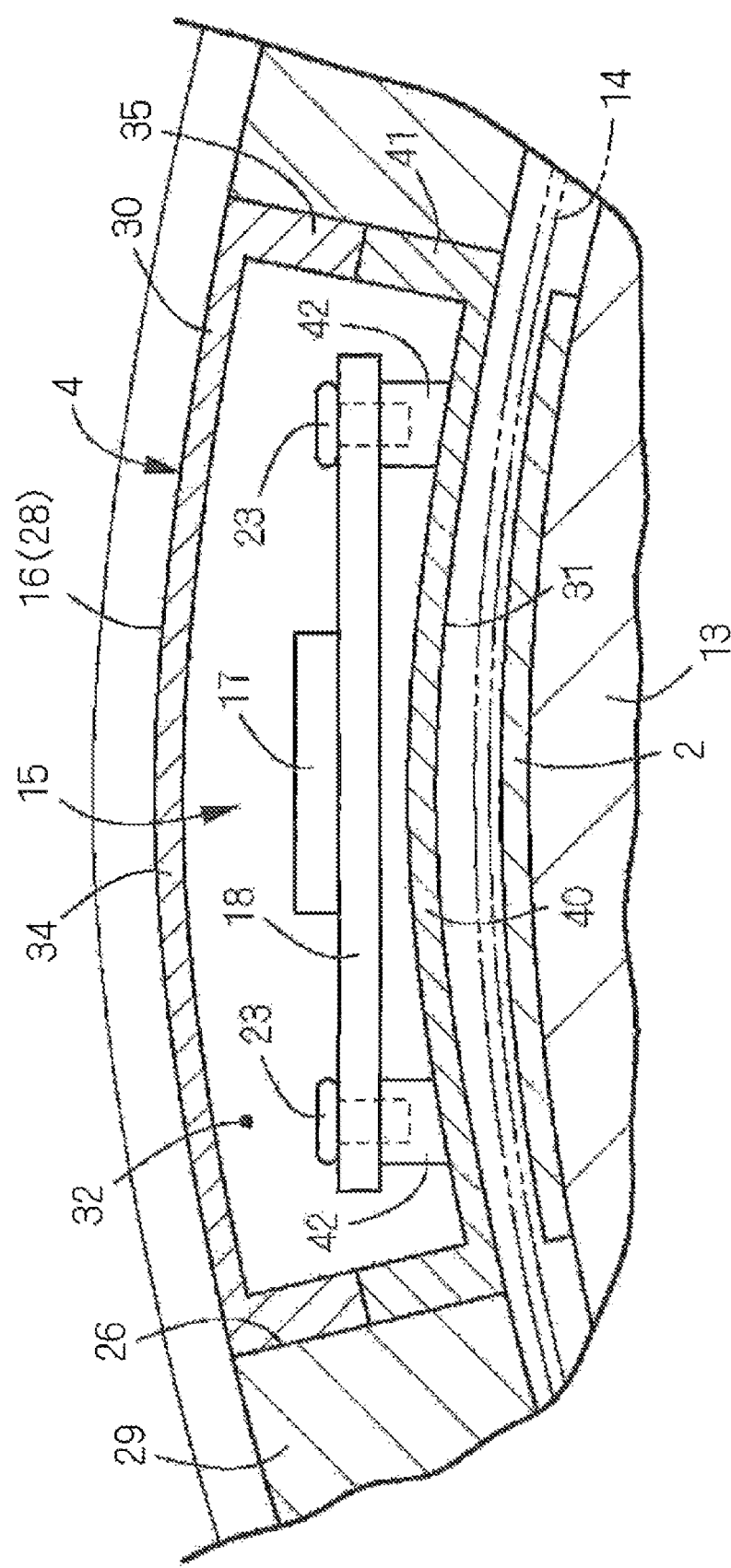
FIG. 6 is a longitudinal sectional side view of the implantable device.
Figure 7:
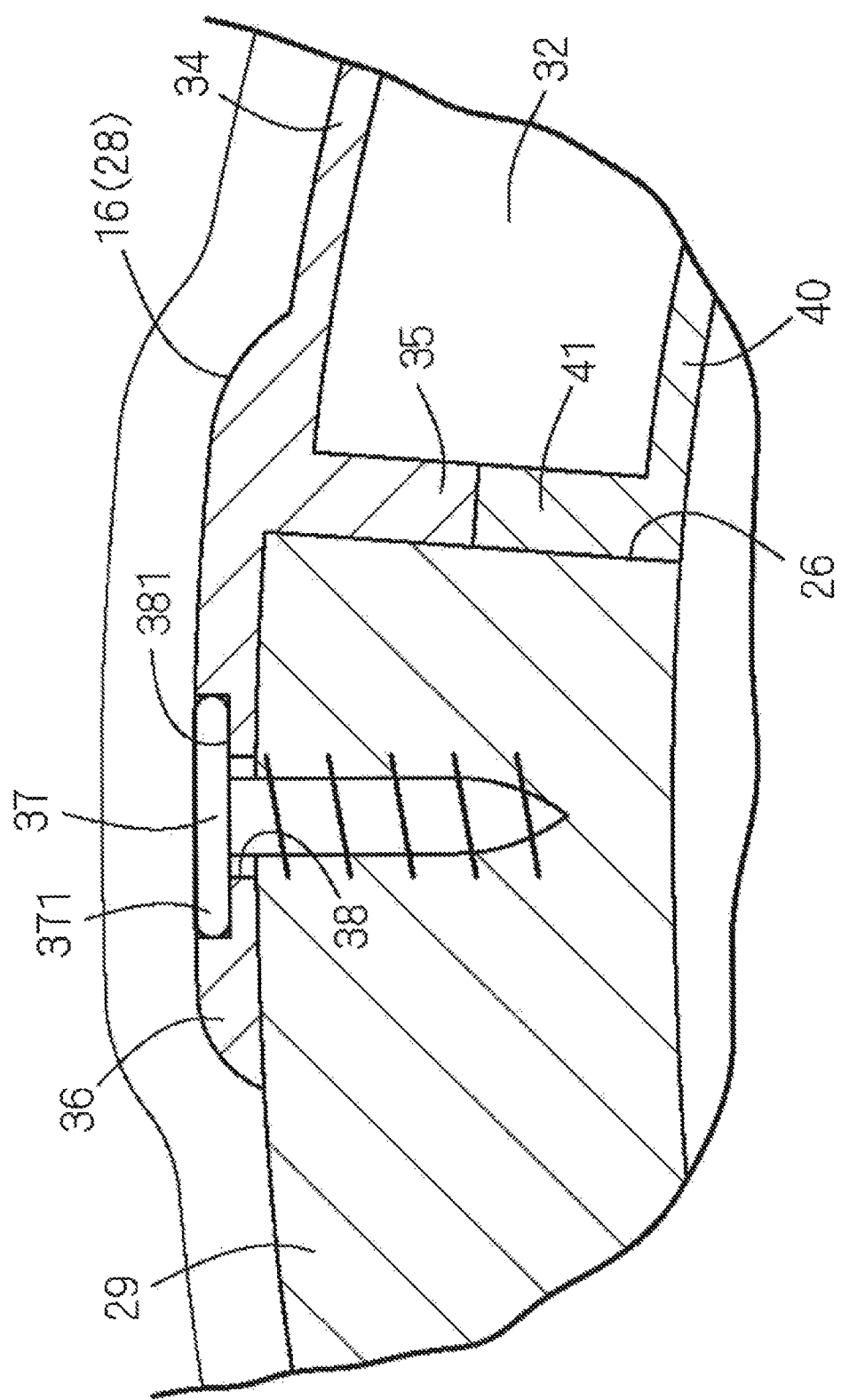
FIG. 7 is a longitudinal sectional front view of a main part.

The outer convexity surface 30 includes an external wall 34 and a rectangular frame-shaped side wall 35 and is formed in the shape of a bottomed container having an aperture at the bottom. The external wall 34 has a shape matching the external shape of the resected skull 27 and is formed to be roughly rectangular in a plan view. The rectangular frame-shaped side wall 35 is vertically disposed down from the four edges of the external wall 34. Fixing plates 36 are formed in a manner being integral with the four corners of the external wall 34 and protruding therefrom in the lateral outward directions (the directions shown by arrows seen in FIG. 4). Formed on the fixing plates 36 are screw insertion holes 38 into which set screws 37 (see FIG. 7) for fixing the implantable device 4 to the skull are to be inserted from above. As shown in FIG. 7, the fixing plates 36 are formed in a stepped manner so that the bottom surfaces thereof are located out of (above) the outer surface of the external wall 34. As shown in FIGS. 6 and 7, when the artificial bone 28 is placed in the craniotomy site 26 of the skull 29, the fixing plates 36 are hooked on the periphery of the craniotomy site 26 of the skull 29. This prevents the artificial bone 28 from unexpected displacement. As shown in FIGS. 1 and 6, the artificial bone 28 placed in the craniotomy site 26 does not cause difference in level between the outer surface (curved surface) of the external wall 34 and the outer surface (curved surface) of the periphery of the craniotomy site 26 of the skull 29. As shown in FIG. 7, the set screws 37 are flat screws, and caving depressions 381 for preventing screw heads 371 from protruding outwardly (upwardly in the illustrated example) are formed in a stepped and depressed manner around the screw insertion holes 38 of the fixing plates 36. The set screws 37 are not limited to flat screws. In short, the set screws 37 may be any type of screws unless the heads thereof protrude from the caving depressions 381.

The inner convexity surface 31 includes an internal wall 40 and a rectangular frame-shaped side wall 41 and is formed in the shape of a bottomed container having an aperture at the top. The internal wall 40 has a shape matching the internal shape of the resected skull 27 and is formed to be roughly rectangular in a plan view. The rectangular frame-shaped side wall 41 is vertically disposed up from the periphery of the internal wall 40. The inner convexity surface 31 and the outer convexity surface 30 are joined together by welding the respective side walls 41, 35 together with the side walls 41, 35 butted together. Thus, the artificial bone 28 matching the shape of the resected skull 27 at the craniotomy site 26 can be obtained. As shown in FIGS. 1 and 4, a total of eight fixing bosses 42 for fixing the electronic circuit 15 using a screw are provided on the internal wall 40 of the inner convexity surface 31 toward the inside of the artificial bone 28 (upwardly in the illustrated example) in a protruding manner (note that the present invention does not limit the number of the fixing bosses 42 to eight). By aligning the through holes 24 formed on the circuit board 18 of the electronic circuit 15 with the corresponding fixing bosses 42 and then screwing the screws 23 into the fixing bosses 42 from above the circuit board 18, the circuit boards 18 can be fixed to the inner convexity surface 31. As shown in FIG. 1, the electronic circuit 15 is placed within the internal space 32 of the artificial bone 28 (casing 16) with the two circuit boards 18 (181, 182) bent in the form of "an inverted V" via the connection made by the flexible printed wiring 19.

As shown in FIGS. 1 and 4, a cable hole 44 for drawing the analog cable 3 into the artificial bone 28 is formed on the inner convexity surface 31. The analog cable 3 and the vicinity of the aperture of the cable holes 44 are sealed by a gasket 45 made of a silicon resin or the like, preventing entry of body fluid into the artificial bone 28. Similarly, a cable hole 46 for drawing the digital cable 5 into the artificial bone 28 is formed on the outer convexity surface 30. The digital cable 5 and the vicinity of the aperture of the cable holes 46 are sealed by a gasket 47.

The internal transceiver 6 configured to be implanted subcutaneously in the abdomen includes a controller, a battery, a wireless transceiver, and an antenna. The controller includes a central controller, a ROM, a RAM, and like and controls the entire system on the basis of a system program stored in the ROM. Specifically, the internal transceiver 6 wirelessly transmits neural signal data transmitted by the implantable device 4 via the digital cable 5, to the external transceiver 7 via an antenna. It also transmits control signals to the implantable device 4 via the digital cable 5. Further, the internal transceiver 6 stores electric power obtained by a non-contact power supply system (wireless power supply) in the battery, as well as supplies the electric power to the implantable device 4 via the digital cable 5. Examples of the non-contact power supply system include an electromagnetic induction system and a magnetic resonance system, or the like.

The external transceiver 7 receives the neural signal data from the internal transceiver 6 and transmits the neural signal data to the computer 8 via the wireless transceivers 10, 11. Eventually, the neural signal data obtained by the sheet-shaped grid electrode array 2 and the implantable device 4 is displayed on the display screen of the computer 8.

As seen, in this embodiment, the artificial bone 28 having a shape matching the resected skull 27 at the craniotomy site 26 is used as the casing 16 of the implantable device 4. Accordingly, the implantable device 4 that is excellent in practical utility and versatility can be obtained without impairing cosmeticity. Further, the artificial bone 28 having strength required and sufficient to fill the craniotomy site 26 is used as the casing 16 of the implantable device 4. Accordingly, the implantable device 4 that is excellent in impact resistance or the like can be obtained. Furthermore, the electronic circuit 15 of the implantable device 4 is placed within the internal space 32 of the artificial bone 28. Thus, there is no possibility that such as unexpected displacement of the electronic circuit 15 may occur. As a result, the implantable device 4 that is reliable can be obtained.

Further, the electronic circuit 15 is divided into the two circuit boards 181, 182, and both circuit boards, 181 and 182, are connected by the flexible printed wiring 19. Thus, the electronic circuit 15 can be placed within the internal space 32 with the electronic circuit 15 bent. Thus, the electronic circuit 15 can be placed within the narrow internal space 32. As a result, unnecessary upsizing of the artificial bone 28 (casing 16) can surely be prevented. Further, the implantable device 4 configured to convert analog signals into digital signals is disposed adjacent to the sheet-shaped grid electrode array 2, so that the length dimension of the analog cable 3 is reduced as much as possible. Thus, occurrence of noise can effectively be reduced, constructing a system having excellent recording accuracy with high signal-to-noise ratio.

Second Embodiment

Figure 11:
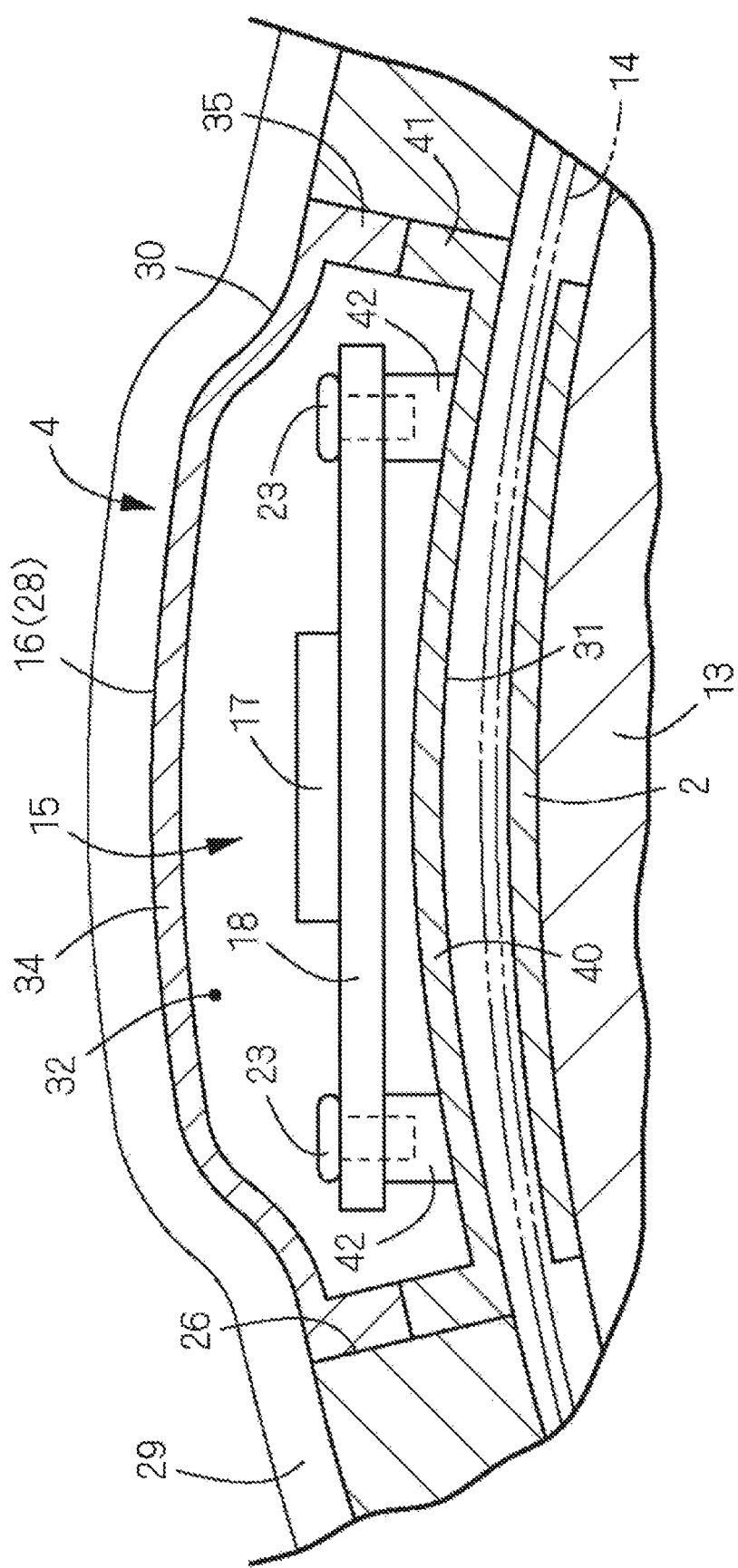
FIG. 11 is a longitudinal sectional front view showing main parts of an implantable device and a casing according to a second embodiment.
Figure 12:
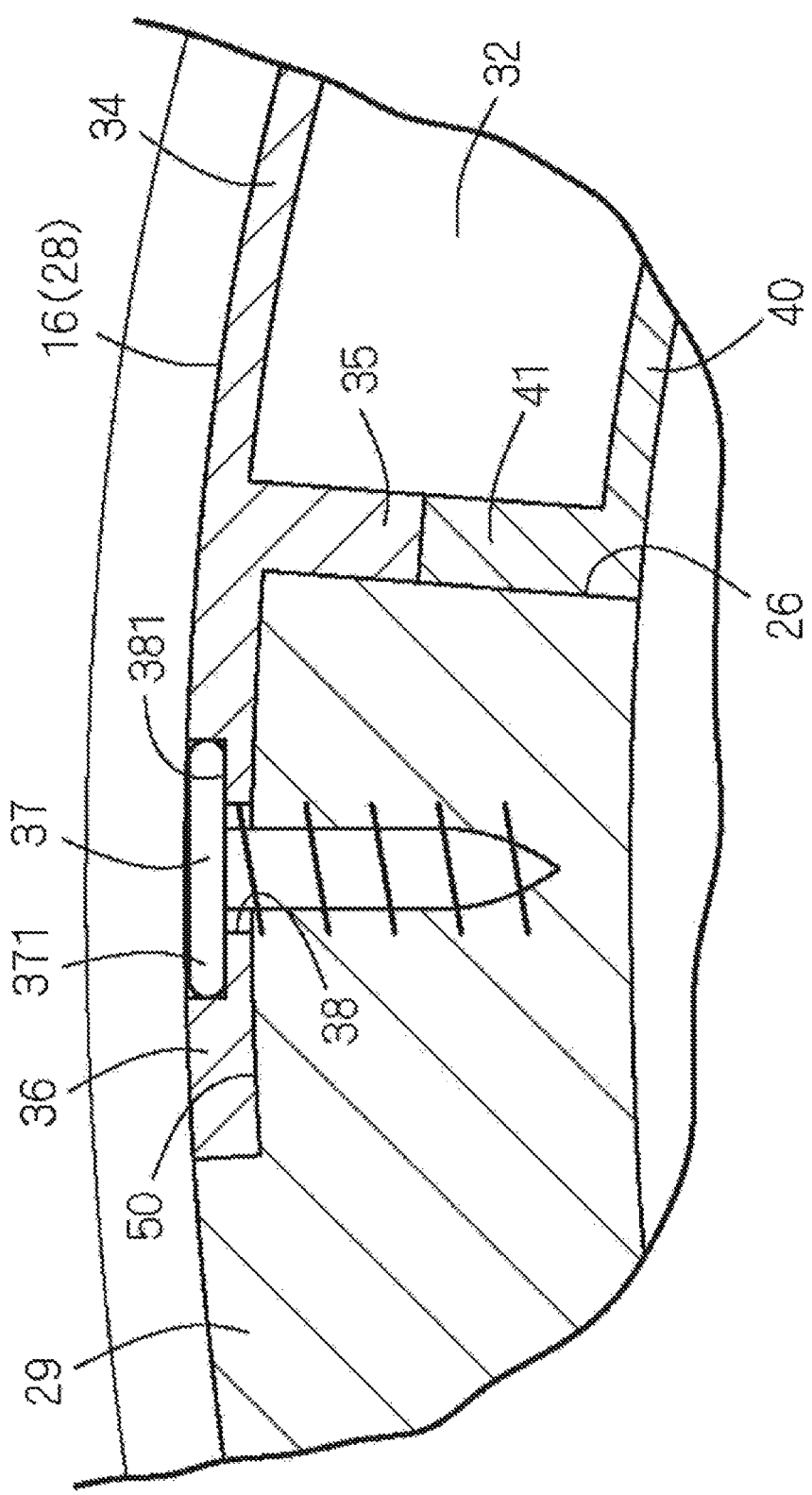
FIG. 12 is a longitudinal sectional side view showing main parts of the implantable device and the casing according to the second embodiment.

FIGS. 11 and 12 show a second embodiment of the present invention. The second embodiment differs from the first embodiment in the following point: in the case where when, in designing the layout using CAD, the skull shape of the patient is used as the shape of a casing outer convexity surface 30 as it is, an electronic circuit 15 cannot be laid out within internal space 32 of a casing 16, the outer convexity surface 30 is formed in a manner swelling out slightly outwardly (upwardly in the illustrated example) so as to secure internal space 32 sufficient to incorporate the electronic circuit 15 (FIG. 11). Further, the second embodiment differs from the above-mentioned first embodiment in that the top surfaces of fixing plates 36 are flush with the top surface of an external wall 34 and in that caving depressions 50 to which the fixing plates 36 are to be attached are formed on a skull 29 around a craniotomy site 26 in the shape of notches (FIG. 12). The second embodiment is the same as the above-mentioned first embodiment in the other points. Accordingly, same components are assigned same signs and will not be described.

Figure 13:
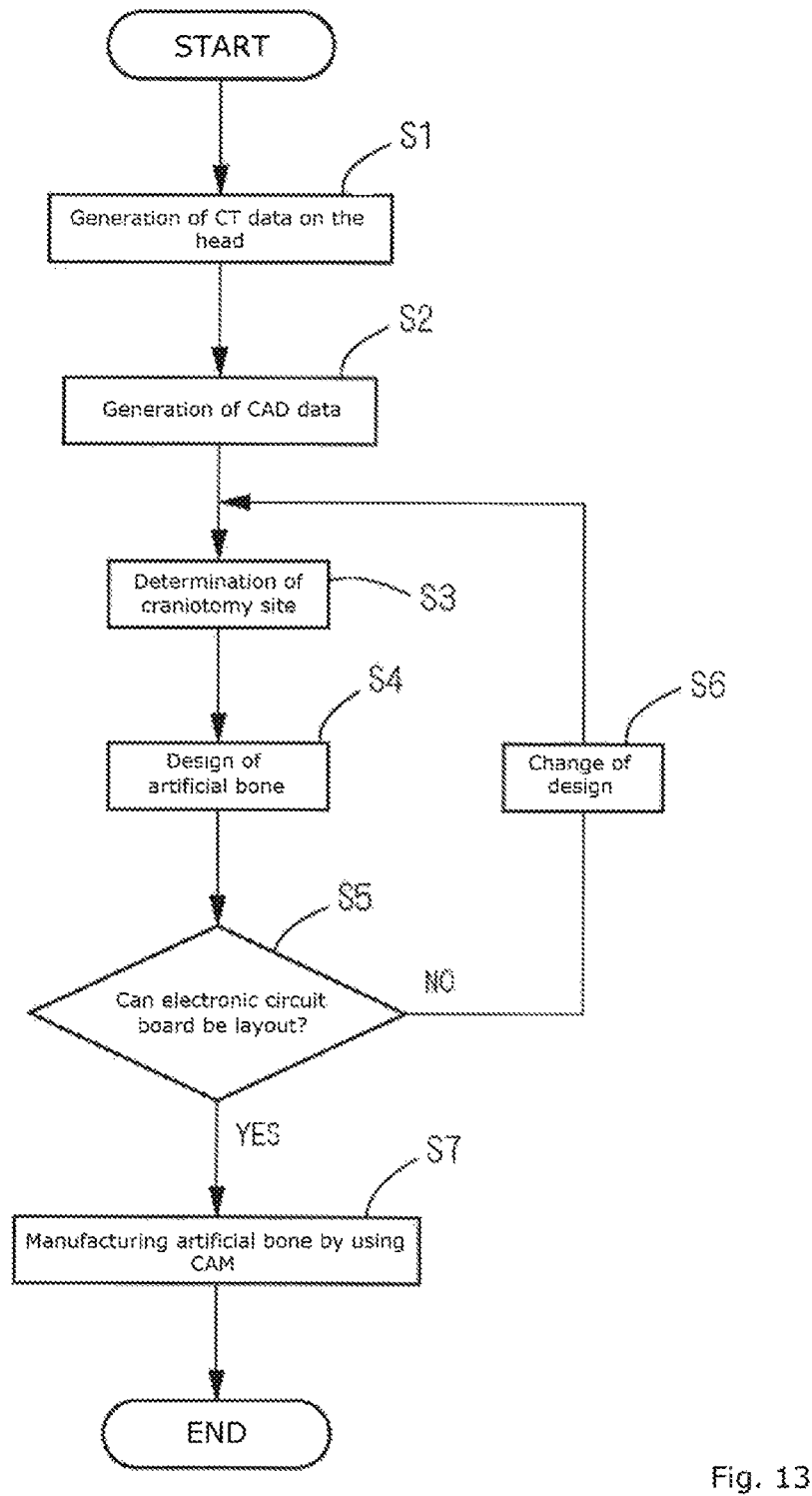
FIG. 13 is a flowchart showing a method for manufacturing a casing of an implantable device.

FIG. 13 shows a method for manufacturing the casing 16 of the implantable device 4 according to the present invention. First, a thin slice CT scan is conducted on the patient, and detailed CT data on the head of the patient is generated (S1). Then, CAD data is generated by converting the CT data into CAD data (S2). Note that if the CT data can be handled using CAD, step S2 is not required. Subsequently, after the craniotomy site 26 is determined using CAD considering various factors such as the functional anatomy of the brain, the position of the affected site, the layout position of the sheet-shaped grid electrode array 2, and the state of the skull 29 (S3: craniotomy site determination step, see FIG. 9), the artificial bone 28 (casing 16) matching the shape of the resected skull at the craniotomy site 26 is designed (S4: artificial bone design step). Specifically, considering such as the thickness dimension of the resected skull 27 and the thickness dimensions of the internal wall 40, the external wall 34, and the side walls 35, 41 forming the artificial bone 28, the shape of the artificial bone 28 (casing 16) matching the shape of the resected skull 27 is determined. Further, the artificial bone 28 is divided into the outer convexity surface 30 and the inner convexity surface 31, and the internal space 32 is formed therebetween. The thickness dimensions of the internal wall 40, the external wall 34, and the like are determined mainly in terms of securing of the strength of the artificial bone 28.

Subsequently, it is checked using CAD whether the electronic circuit 15 can be laid out within the internal space 32 (S5: electronic circuit circuit board layout check step). This check step includes checking whether the entire electronic circuit 15 can be laid out without contacting the inner convexity surface 31 or the outer convexity surface 30, while adjusting such as the bending angles of both circuit boards, 181 and 182, and the height dimension of the fixing bosses 42. This check step also includes checking whether the cables 3, 5 can be connected to the connectors 21, 22, respectively, mounted on the circuit boards 181, 182.

If it is determined in the check step S5 that the electronic circuit 15 cannot be laid out within the internal space 32 (S5: NO, S6), the process returns to S3, and the determination of the craniotomy site 26 and the design of the artificial bone 28 (casing 16) are repeated. Alternatively, the process may return not to S3 but to S4 to swell out the outer convexity surface 30 slightly outwardly (see FIGS. 11, 12).

If it is determined in the check step S5 that the electronic circuit 15 can be laid out within the internal space 32 (YES in S5), the design of the artificial bone 28 (casing 16) is completed. Subsequently, cutting processing is performed using CAM on the basis of the designed CAD data to manufacture the artificial bone 28 (S7). Specifically, cutting processing is performed on a titan block to cut out the outer convexity surface 30 and the inner convexity surface 31. Specifically, the artificial bone 28 is manufactured using the generated CAM data and a number-controlled cutting processor. The artificial bone 28 is also able to be manufactured using 3D printing technology such as selective laser melting method, direct metal laser sintering method and the like, based on CAD data. Subsequently, the electronic circuit 15 and the like are placed within the artificial bone 28, and the outer convexity surface 30 and the inner convexity surface 31 are welded and joined together. Thus, the implantable device 4 is completed.

In a surgery, a craniotomy is correctly performed on the craniotomy site 26 determined in the above-mentioned craniotomy site determination step (S3) with the aid of a neurosurgical navigation system. After the sheet-shaped grid electrode array 2 is placed on the brain 13 (on the cerebral cortex), the implantable device 4 is placed within the craniotomy site 26 and fixed to the skull 29 using the set screws 37 to fill the craniotomy site 26.

The function unit according to the present invention is not limited to the sheet-shaped grid electrode array 2 shown in the above-mentioned embodiments and may be a sheet-shaped grid electrode array for neural stimulation. Specifically, the implantable device 4 according to the present invention is also applicable to brain stimulators such as deep brain stimulators and cerebral stimulators, drug infusion systems, and tissue cooling systems.

In the above-mentioned embodiments, the entire artificial bone 28 having the outer convexity surface 30 and the inner convexity surface 31 is used as the casing 16 of the implantable device 4. However, the present invention is not limited thereto and only the outer convexity surface 30 may be used as the casing 16. In this case, there is a need for a measure to secure hermeticity of the electric circuit, such as packaging of the electronic circuit 15.

The craniotomy site is not limited to that shown in the above-mentioned embodiment. Further, the installation site is not limited to the skull. The artificial bone 28 can be installed on any bone if the bone is a relatively large bone such as a long bone, including the femur and the humerus, and the pelvis, and the breast bone. That is, the essence of the present invention is to allow the artificial bone to house the circuit and thus have both a bone function and a casing function.

While the electronic circuit 15 is divided into the two circuit boards 18 (181, 182) in the above-mentioned embodiment, it may be divided into three or more circuit boards 18. However, if the electronic circuit 15 has a small circuit board 18, there is no need to divide it. While the circuit boards 18 of the electronic circuit 15 are fixed using screws in the embodiment, the present invention is not limited to this fixing form. A configuration may be used where the electronic circuit 15 is fixed to the artificial bone 28 (casing 16) using an adhesive or the like. A configuration may be used where the electronic circuit 15 is placed within the internal space 32 with the circuit board 18 coated with a resin or the like. The configuration where the outer convexity surface 30 and the inner convexity surface 31 are welded and joined together, as well as a configuration where these surfaces are joined together using an adhesive may be used. Further, after welding and joining the surfaces together, the junction thereof may be filled with an adhesive.

Third Embodiment

FIGS. 14 to 23 show a third embodiment where an implantable device according to the present invention is applied to a brain signal measurement system. This brain signal measurement system is similar to the system according to the above-mentioned first embodiment shown in FIG. 2. It includes a sheet-shaped grid electrode array (function unit) 2 for brain signal (electrocorticogram) measurement, an implantable device 4 connected to the sheet-shaped grid electrode array 2 via an analog cable (cable) 3, an internal transceiver 6 connected to the implantable device 4 via a digital cable 5 and implanted subcutaneously in the abdomen, an external transceiver 7 wirelessly connected to the internal transceiver 6, and a personal computer (hereafter simply referred to as "computer") 8 for neural signal processing.

Figure 14:
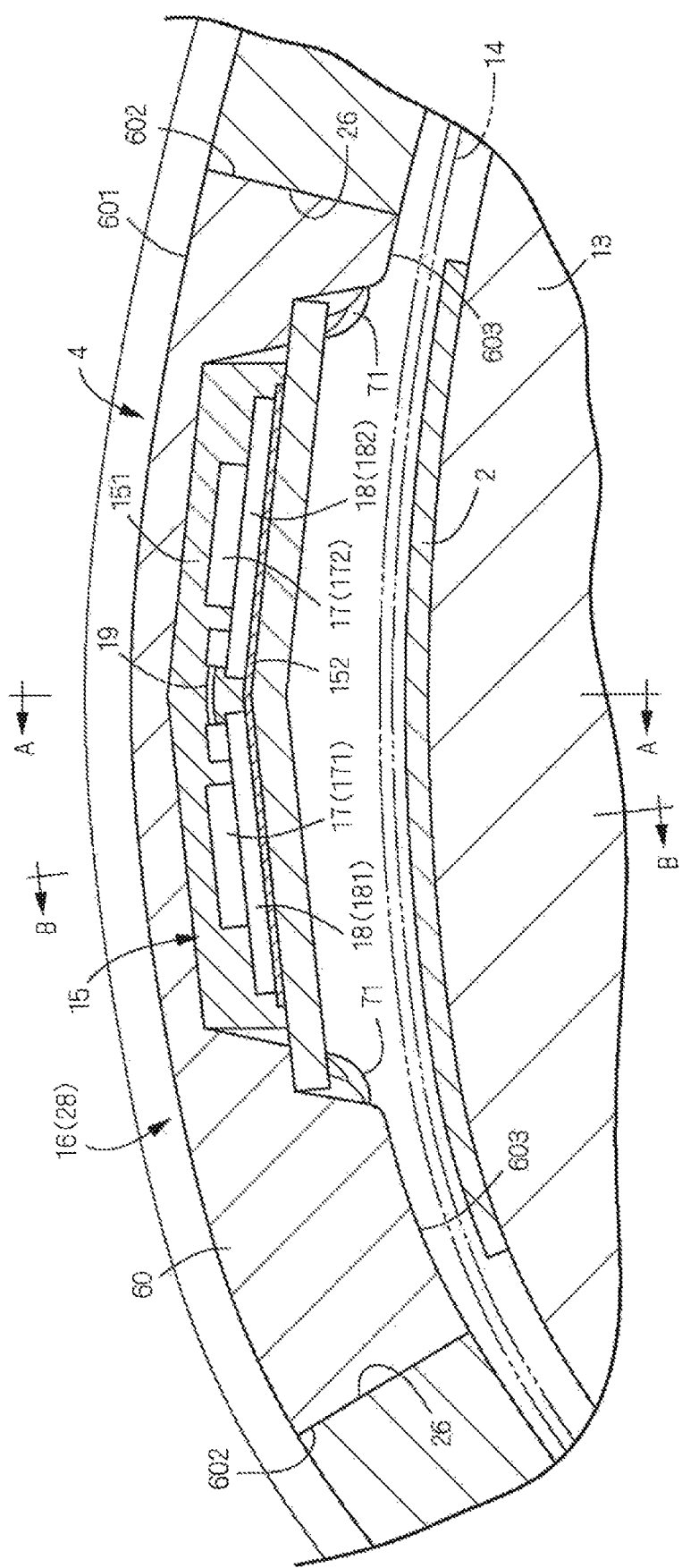
FIG. 14 is a longitudinal sectional front view showing main parts of an implantable device and a casing according to a third embodiment.
Figure 15:
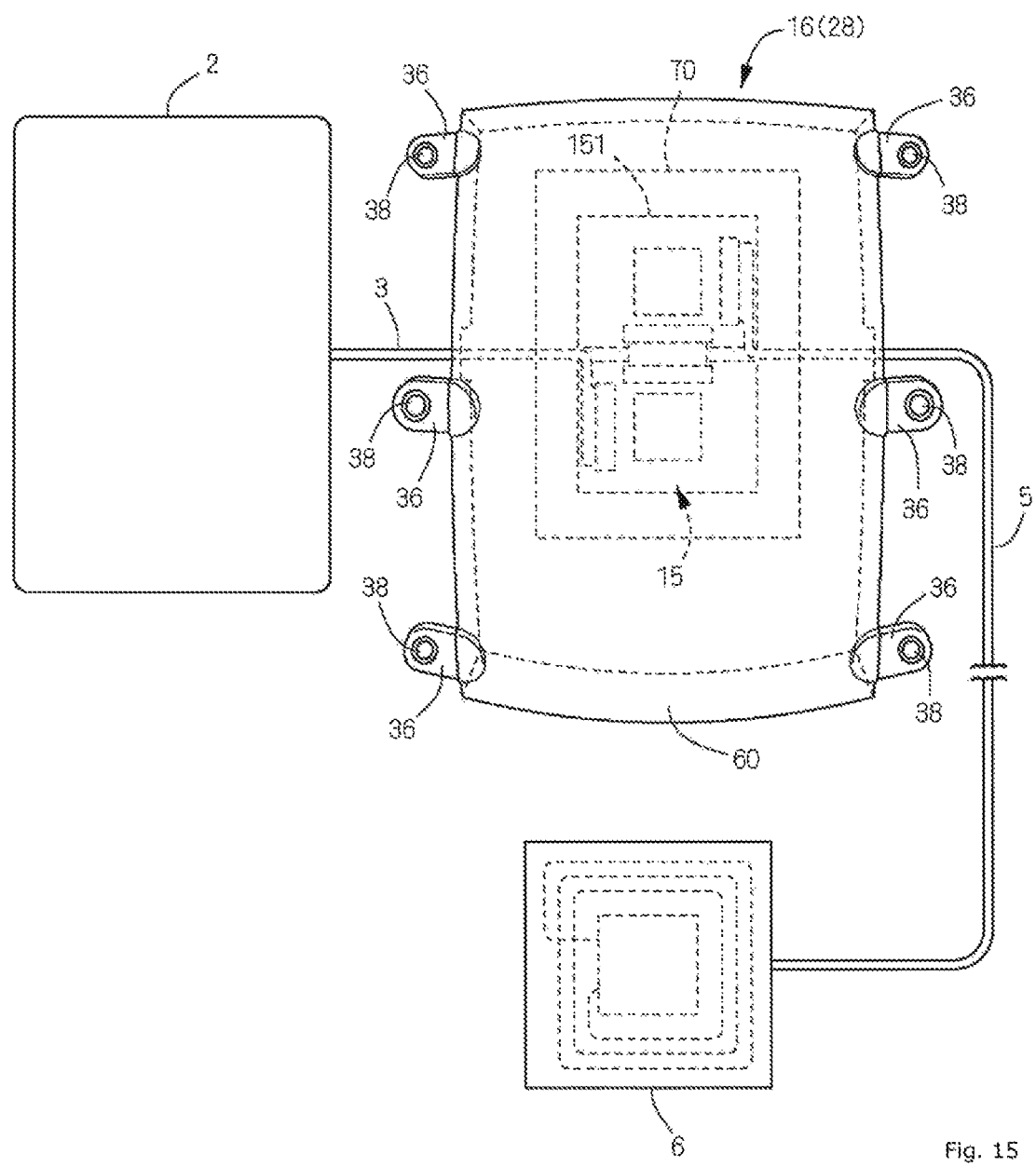
FIG. 15 is plan views of the implantable device, a sheet-shaped grid electrode array, and an internal transceiver.

As shown in FIG. 14, the sheet-shaped grid electrode array 2 is disposed under the dural membrane. In this embodiment, it is fixed to the surface of a brain 13 (the surface of the brain cortex), such as the cerebral cortex. The sheet-shaped grid electrode array 2 is a high-density electrode in which many electrodes are disposed with high density and measures electrocorticograms at many points on the surface of the brain 13. As shown in FIG. 15, an electrocorticographic signals measured by the sheet-shaped grid electrode array 2 is transmitted to the implantable device 4 via the analog cable 3 while remaining an analog signal. Examples of the analog cable 3 include a 128-wire cable.

Figure 16:
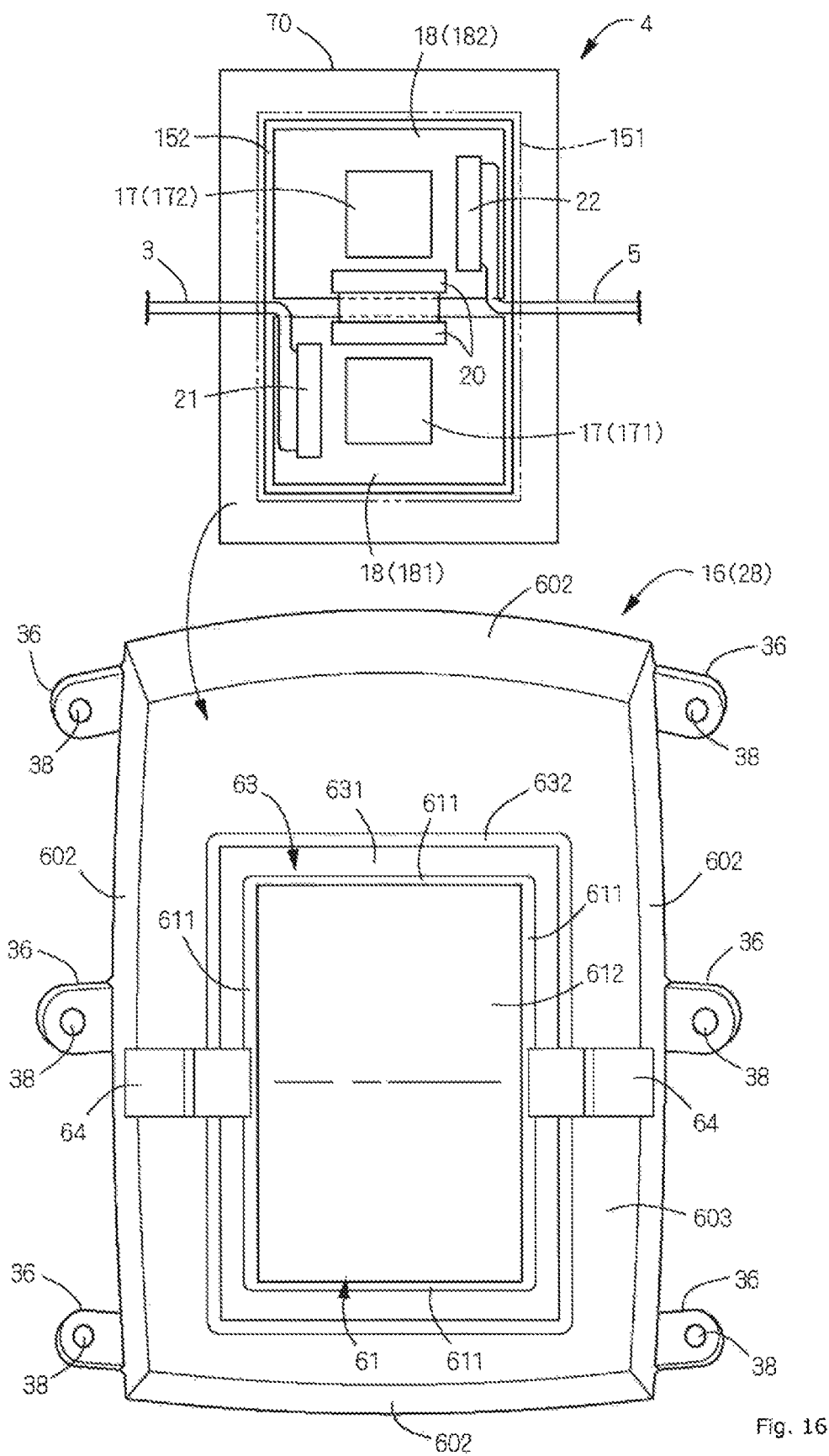
FIG. 16 is an exploded plan view of the implantable device.
Figure 17:
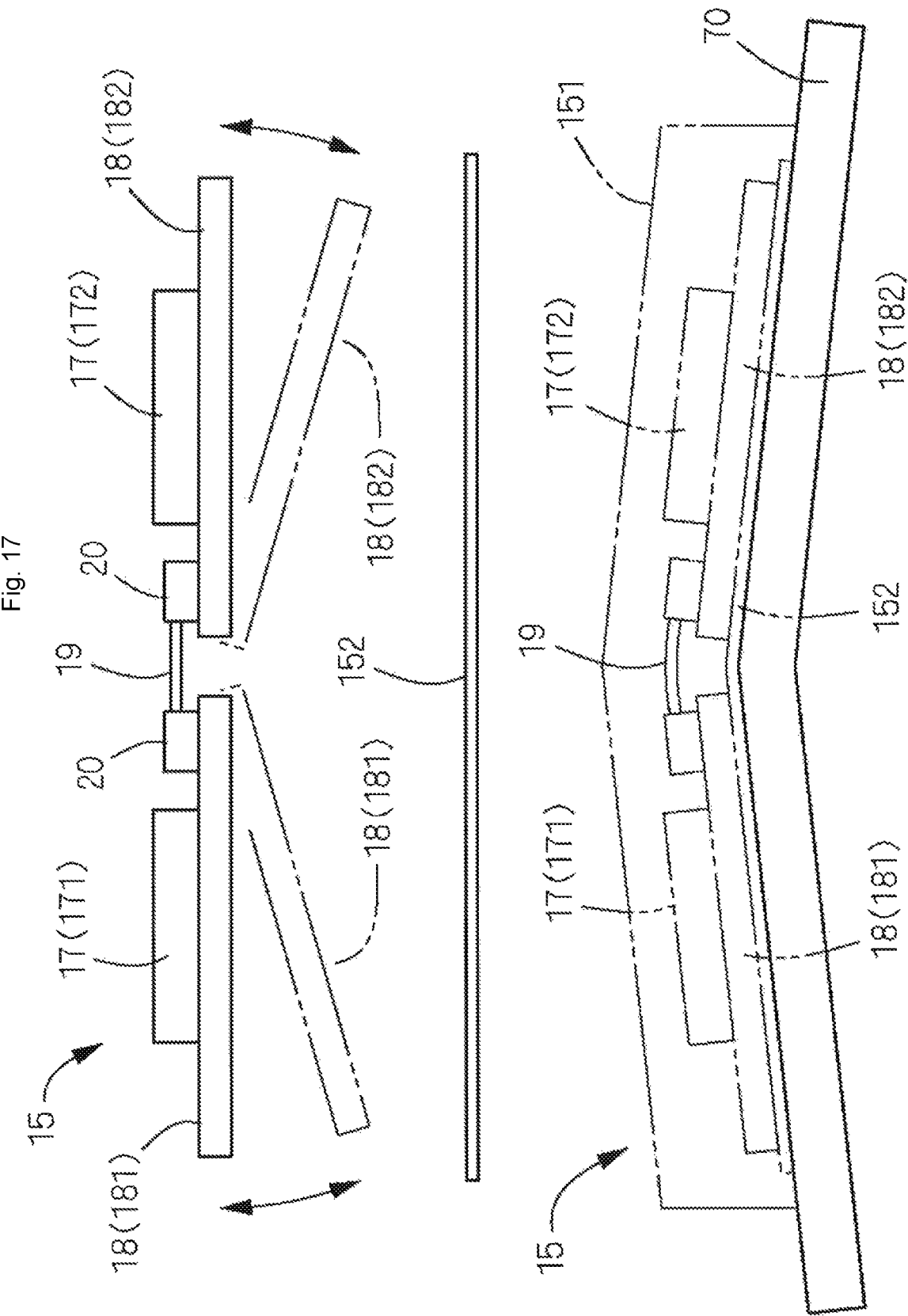
FIG. 17 is a diagram showing an electronic circuit included in the implantable device and a cover plate for supporting the electronic circuit.

The implantable device 4 is fixed adjacent to the sheet-shaped grid electrode array 2. In this embodiment, it is fixed above the sheet-shaped grid electrode array 2 in the brain. The implantable device 4 amplifies and digitizes the measured signals (analog signals) transmitted by the sheet-shaped grid electrode array 2 via the analog cable 3. It includes an electronic circuit 15 and a casing 16 enclosing the electronic circuit 15. The electronic circuit 15 amplifies the analog signals (measured signals) transmitted by the sheet-shaped grid electrode array 2. It includes IC chips (semiconductor chips) 17 configured to perform such as a process of amplifying the analog signals (measured signals) transmitted by the sheet-shaped grid electrode array 2 and converting the amplified analog signals into digital signals and a process of transmitting the digital signals to the internal transceiver 6 and circuit boards 18 on which the chips 17 are mounted. The electronic circuit 15 according to this embodiment includes two rectangular circuit boards, 181 and 182, IC chips 171, 172 mounted on the rectangular circuit boards 181, 182, respectively, and a flexible printed wiring 19 electrically connecting both circuit boards, 181 and 182. It is configured to be bendable around the connection made by the flexible printed wiring 19. As shown in FIG. 16, connectors 20 for connecting with the flexible printed wiring 19 are mounted on the opposite sides of both circuit boards, 181 and 182. While the circuit board 181 has a connector 21 for connecting with the analog cable 3 mounted thereon, the circuit board 182 has a connector 22 for connecting the digital cable 5 mounted thereon. Note that the electronic circuit 15 and the connectors 20, 21, 22 are fixed to the top surface of a cover plate 70 included in the casing 16 and then placed within the casing 16 as molded using a sealing resin. In FIGS. 14 to 16, FIG. 18, and FIGS. 21, 22, sign 151 represents a molded portion made of a sealing resin. In FIGS. 14 to 18 and FIGS. 21, 22, sign 152 represents a non-conductive spacer disposed between the circuit boards 18 (181, 182) and the cover plate 70.

Figure 20:
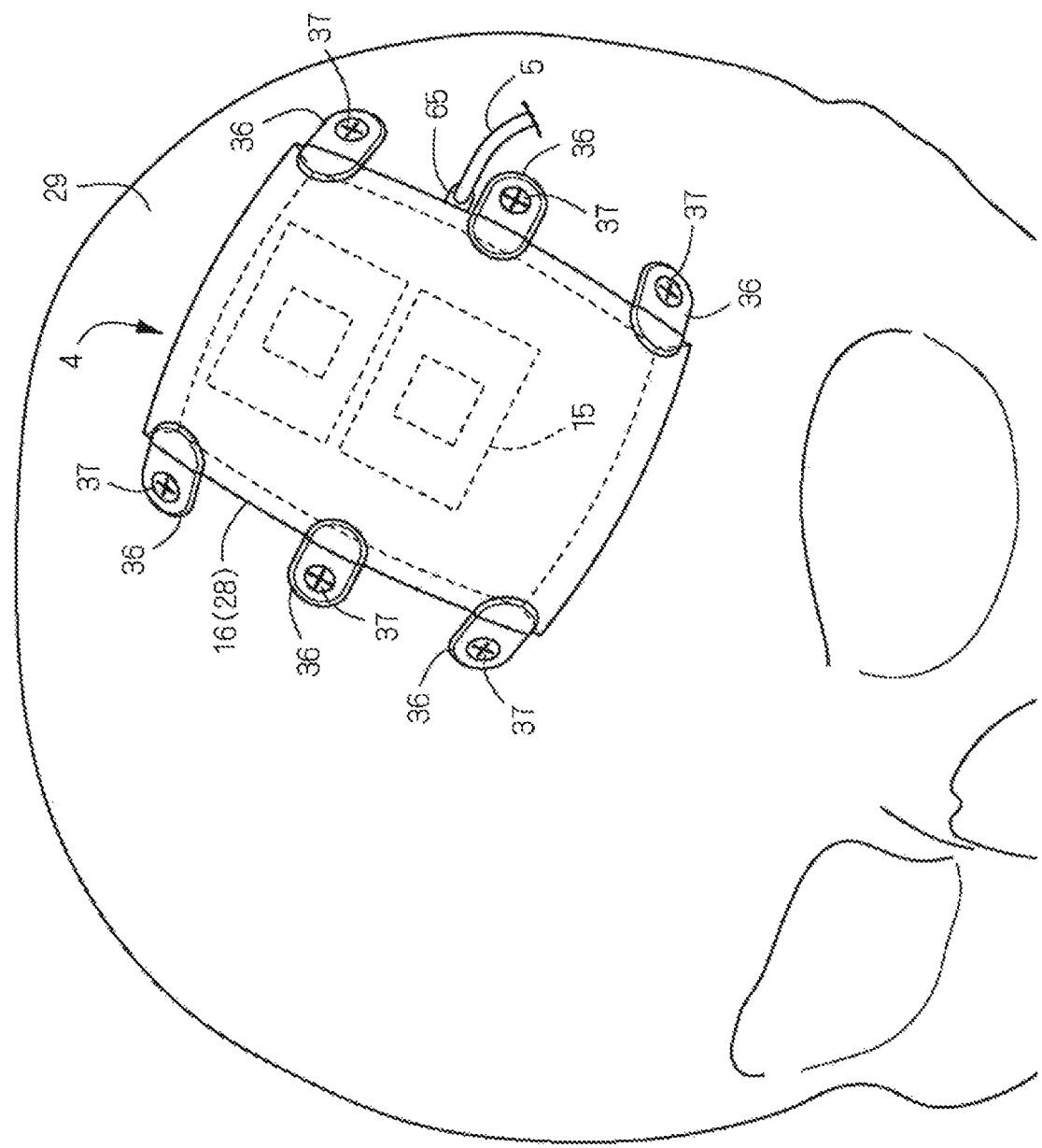
FIG. 20 is a drawing showing a method for fixing the implantable device to the skull.

The implantable device 4 uses, as the casing 16, an artificial bone 28 having a shape matching a resected skull 27 at a craniotomy site 26 and configured to be implanted to fill the craniotomy site 26 (see FIG. 20 and FIG. 8 of the first embodiment). Specifically, the implantable device 4 uses, as the casing 16, the artificial bone 28 configured to be placed within the craniotomy site 26 of a human skull 29 instead of the resected skull 27 after a neurosurgery.

Figure 23:
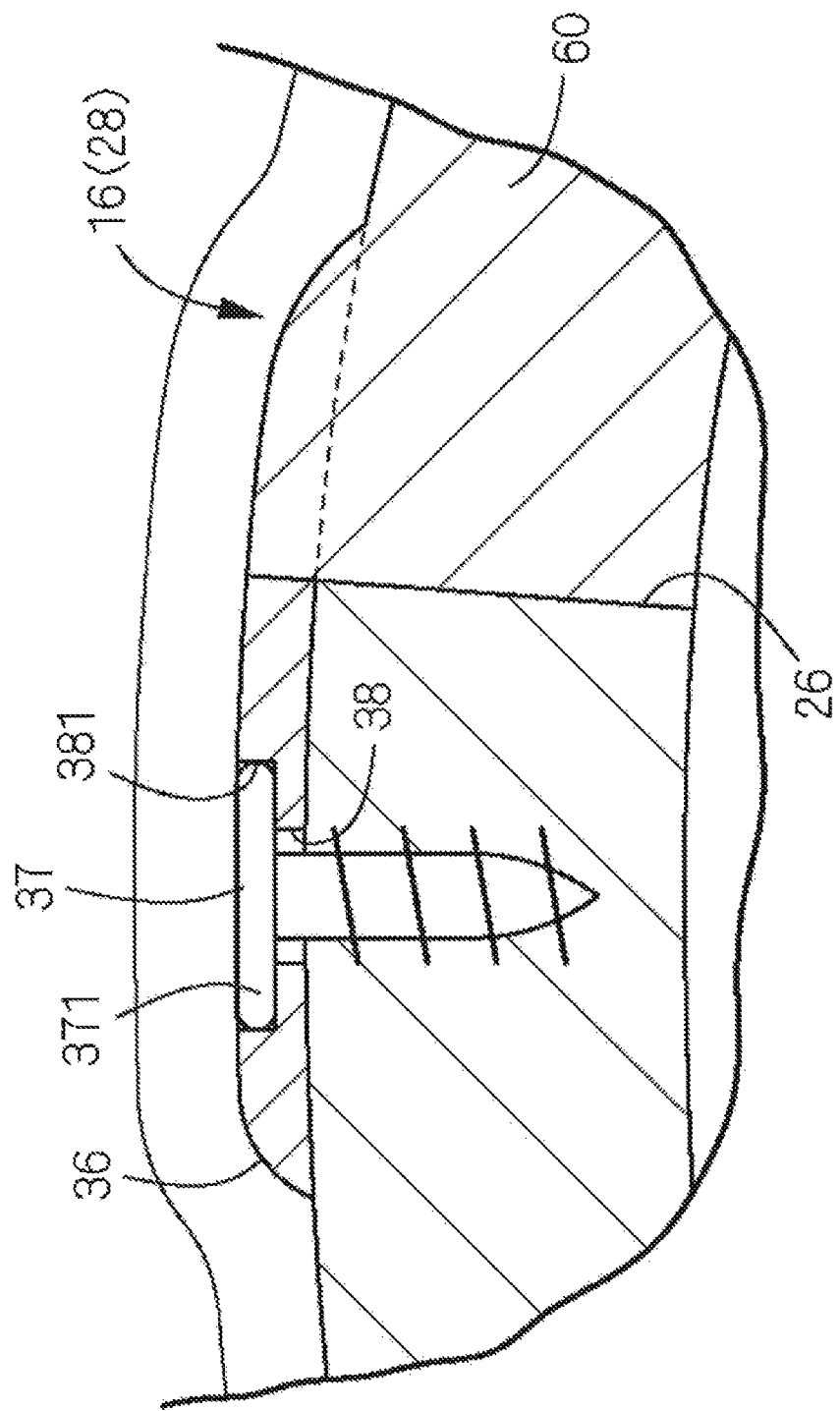
FIG. 23 is a drawing showing an aspect where the implantable device is fixed to the skull.

As shown in FIGS. 14, 16, 18, and 19, the artificial bone 28 includes a convexity 60 having a housing depression 61 into which the electronic circuit 15 is to be inserted and a flat cover plate 70 that is welded and fixed to the periphery of an aperture 62 so that the aperture 62 of the housing depression 61 is filled. The convexity 60 is a machining product cut out from a titanium block or a titanium product formed by a 3D printer. It has an outer surface 601 matching the external shape of the resected skull 27 related to the craniotomy site 26, a side surface 602 matching the side surface shape of the resected skull 27, and an inner surface 603 matching the internal shape of the resected skull 27. In this embodiment, as shown in FIG. 9, the resected skull 27 is formed to be roughly rectangular in a plan view. The outer surface 601 of the convexity 60 is formed to be roughly rectangular in a plan view in accordance with the resected skull 27. A total of six fixing plates 36 are outwardly welded and fixed to the four corners of the convexity 60 and the centers of the long sides thereof. Formed on the fixing plates 36 are screw insertion holes 38 into which set screws 37 for fixing the implantable device 4 to the skull are to be inserted from above. As shown in FIG. 23, the fixing plates 36 are formed in a stepped manner so that the bottom surfaces thereof are positioned out of (upward) the outer surface. When the artificial bone 28 is placed in the craniotomy site 26 of the skull 29, the fixing plates 36 are hooked onto the periphery of the craniotomy site 26 of the skull 29, preventing the artificial bone 28 from falling down. As shown in FIG. 14, in a state where the artificial bone 28 is placed in the craniotomy site 26, the curved surface of the external surface 601 of the convexity 60 and the outer surface (curved surface) of the periphery of the craniotomy site 26 of the skull 29 connect with each other smoothly. As shown in FIG. 23, the set screws 37 are flat screws, and caving depressions 381 for preventing screw heads 371 from protruding outwardly (upwardly in the illustrated example) are formed in a stepped and depressed manner around the screw insertion holes 38 of the fixing plates 36. The set screws 37 are not limited to flat screws and, in short, may be any type of screws unless the heads thereof protrude from the caving depressions 381.

Figure 18:
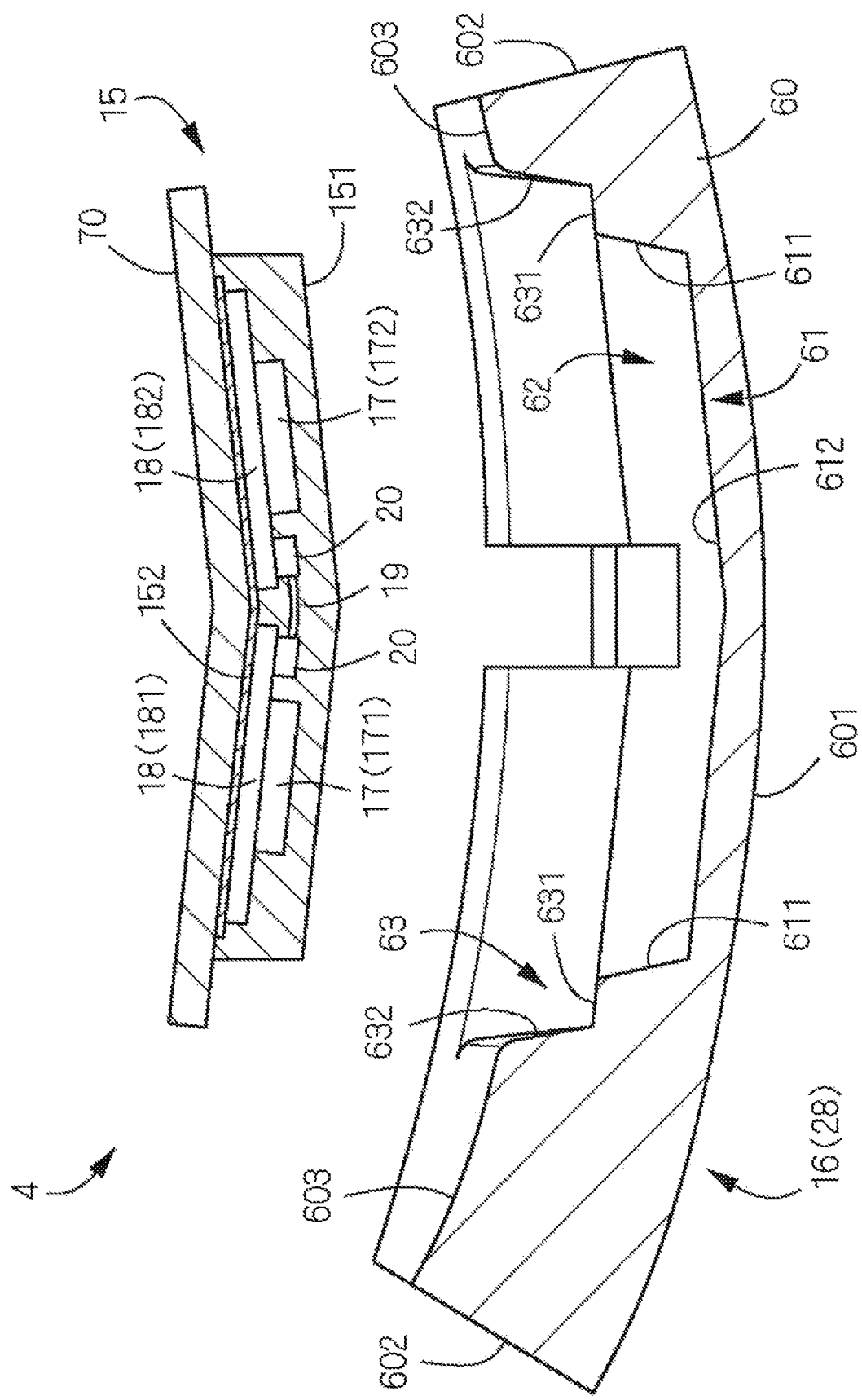
FIG. 18 is a diagram showing a method for mounting a cover plate and an electronic circuit on an outer convexity surface.
Figure 21:
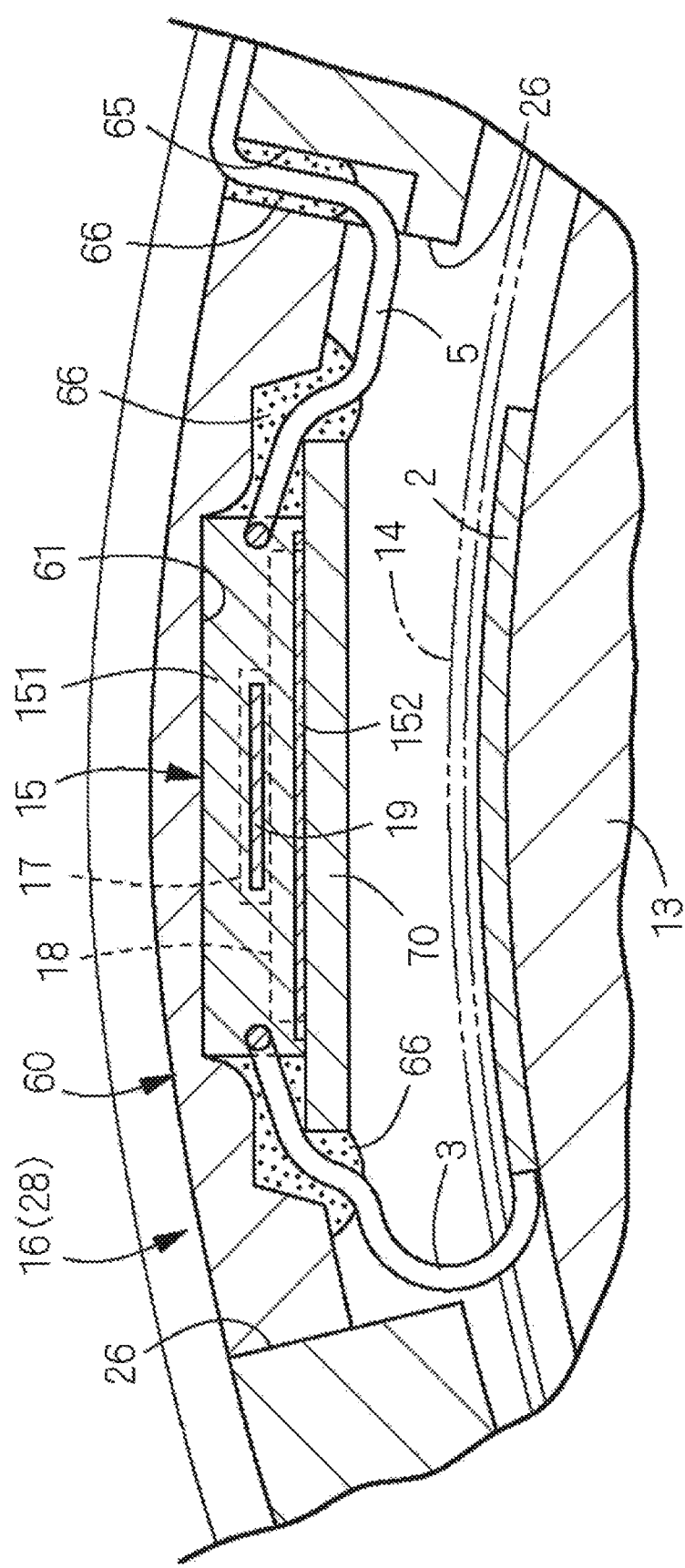
FIG. 21 is a sectional view taken along line A-A of FIG. 14.
Figure 22:
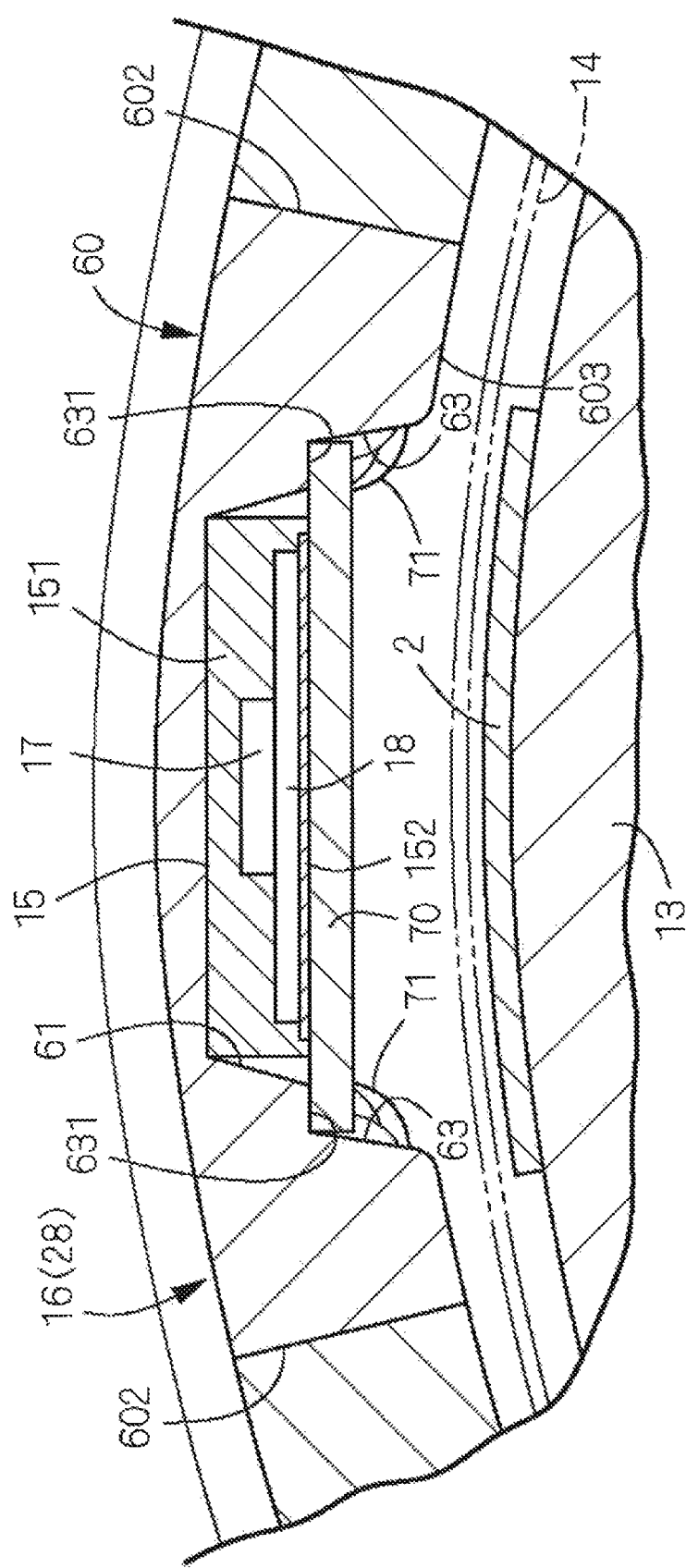
FIG. 22 is a sectional view taken along line B-B of FIG. 14.

As shown in FIG. 14, the edge of the inner surface 603 of the convexity 60 matches the internal shape of the resected skull 27 (see FIG. 9) of the craniotomy site 26. Formed in the surface center of the inner surface 603 of the convexity 60 is a housing depression 61 for housing the electronic circuit 15 molded using a sealing resin. As shown in FIGS. 16 and 18, the housing depression 61 is a bottomed rectangular hole having four side surfaces 611 and a deep end surface 612. Formed on the corners between the inner surface 603 of the convexity 60 and the side surfaces 611 of the housing depression 61 is a rectangular depressed space 63 having a rectangular frame-shaped receiving surface 631 oriented toward the brain. The external dimension of the receiving surface 631 is set as being slightly larger than that of the cover plate 70. The side surfaces 611 of the housing depression 61 and side surfaces 632 of the depressed space 63 are formed in the shape of a bottom-expanded taper which gradually becomes larger as it goes toward the brain (downward). Formed on two regions of the side surface 632 of the depressed space 63 are cable channels 64•64 for drawing the analog cable 3 and the digital cable 5. As shown in FIG. 21, the digital cable 5 drawn from the housing depression 61 via the cable channels 64•64 is drawn above the skull via a cable hole 65 which is formed on the skull 29 as being adjacent to the craniotomy site 26. A sealing resin 66 is filled between the cable channels 64•64, and the cables 3, 5, as well as between the cable hole 65 and the digital cable 5.

Figure 19:
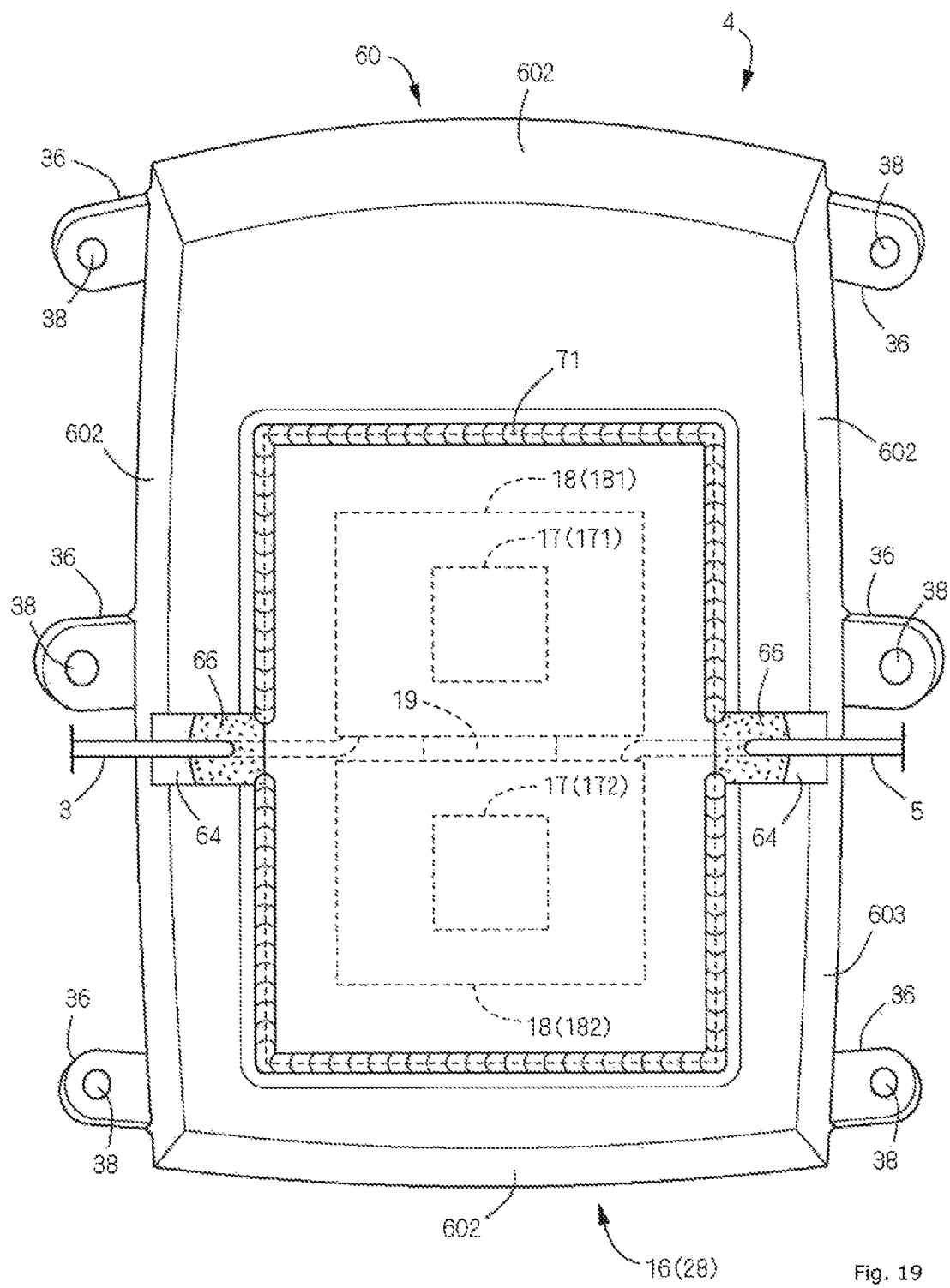
FIG. 19 is a bottom view of the implantable device.

The cover plate 70 is welded and fixed to the periphery of the aperture of the housing depression 61. Specifically, as shown in FIG. 14, by welding the edges of the cover plate 70 to the side surfaces 632 of the depressed space 63 in an insertion state where the edges of the cover plate 70 are received by the receiving surface 631, the cover plate 70 is welded and fixed to the periphery of the aperture of the housing depression 61 of the convexity 60. As shown in FIG. 19, the cover plate 70 is welded and fixed to the entire side surfaces 632 of the depressed space 63 except for the cable channels 64•64. In FIGS. 14 and 19, sign 71 represents weld beads. As seen, by forming the depressed space 63 on the periphery of the housing depression 61 and welding and fixing the edges of the cover plate 70 to the side surfaces 632 of the depressed space 63 with the cover plate 70 received by the receiving surface 631 of the depressed space 63, the swelling weld bead 71 can surely be prevented from protruding from the inner surface 603 of the convexity 60 toward the brain.

As with the convexity 60, the cover plate 70 is a rectangular plate made of titanium or a titanium product formed by a 3D printer. It is welded and fixed to the periphery of the aperture of the housing depression 61 mainly for prevention of entry of liquid components or the like into the housing depression 61. The cover plate 70 also serves as a circuit board for supporting the electronic circuit 15. The electronic circuit 15 is fixed to the cover plate by the steps below. First, the circuit boards 18 (181, 182) where the IC chips 17 (171, 172) and the connectors 20, 21, 22 are mounted and connected together by the flexible printed wiring 19 are fixed to the top surface (the surface oriented to the housing depression 61, of the cover plate 70) of the cover plate 70 using an adhesive with the spacer 152 interposed therebetween. Next, the cables 3, 5, 19 are connected to the connectors 20, 21, 22 and then the entire electronic circuit 15 including the IC chips 17 (171, 172), the connectors 20, 21, 22, the flexible printed wiring 19, and the circuit boards 18 (181, 182) is molded using a sealing resin. In this way, the electronic circuit 15 molded using the sealing resin can be fixed to the top surface of the cover plate 70. The molded portion 151 made of the sealing resin is formed in the shape of a block and covers the entire electronic circuit 15. The thickness dimension of the molded portion 151 is only required to be a dimension covering the entire electronic circuit 15 and is determined considering such as the depression dimension of the housing depression 61.

The artificial bone 28 and the electronic circuit 15 are designed in such a manner that the electronic circuit 15 can be placed within the housing depression 61. Specifically, the positions and sizes of the housing depression 61 and the depressed space 63 of the convexity 60, the shape of the electronic circuit 15 including the molded portion 151, the bend angle of the electronic circuit 15, as well as the shape of the cover plate 70 are all designed mainly for allowing the electronic circuit 15 to be placed within the housing depression 61 successfully. In designing the artificial bone 28 and the electronic circuit 15, particular consideration is given to such as providing, to the convexity 60, sufficient rigidity not to be unexpectedly broken when large external force is applied to the outer surface 601 thereof (that is, providing, to the housing depression 61 formation region, sufficient rigidity because a reduction in the vertical thickness dimension of the convexity 60 cannot be avoided in the housing depression 61 formation region) and preventing the swelling weld bead 71 from protruding from the inner surface 603 of the convexity 60 toward the brain. At this time, if the electronic circuit 15 is configured in such a manner that the two circuit boards 181, 182 are connected by the flexible printed wiring 19 and the electronic circuit 15 can be bent via the connection made by the flexible printed wiring 19, as in this embodiment, the design flexibility of the aperture position of the housing depression 61 of the convexity 60 is considerably increased. The shape of the cover plate 70 is also designed in accordance with the bent shape of the electronic circuit 15. In this embodiment, the electronic circuit 15 is bent in the shape of an inverted V via the connection of the two circuit boards, 181 and 182, made using the flexible printed wiring 19. The cover plate 70 is also bent in the shape of an inverted V in accordance with the bent posture of the electronic circuit 15.

The configurations of the internal transceiver 6 configured to be implanted subcutaneously in the abdomen, the external transceiver 7, and the like are similar to those shown in the above-mentioned first embodiment and therefore will not be described.

As seen, in this embodiment, the artificial bone 28 matching the external shape of the resected skull 27 at the craniotomy site 26 is used as the casing 16 of the implantable device 4. Thus, the implantable device 4 that is excellent in practical utility and versatility can be obtained without impairing the appearance of the patient. Further, since the artificial bone 28 is mainly composed of the block-shaped convexity 60 cut out from a titanium block or a titanium product formed by a 3D printer, the artificial bone 28 serving as the casing 16 of the implantable device 4 can be provided with required and sufficient strength to fill the craniotomy site 26. As a result, the implantable device 4 that is excellent in shock resistance and the like can be obtained. Further, the electronic circuit 15 of the implantable device 4 is placed within the housing depression 61 of the convexity 60 included in the artificial bone 28, and the cover plate 70 is welded and fixed to the periphery of the aperture of the housing depression 61. This eliminates risk for such as unexpected displacement of the electronic circuit 15, allowing the implantable device 4 that is reliable to be obtained.

The electronic circuit 15 is divided into the two circuit boards 181, 182, and both circuit boards, 181 and 182, are connected by the flexible printed wiring 19. Thus, the electronic circuit 15 can be placed within the housing depression 61 in a bent manner. As a result, the electronic circuit 15 can be placed within the narrow internal space 32. This can prevent useless upsizing of the artificial bone 28 (casing 16). Further, the design flexibility of the artificial bone 28 (casing 16) is considerably increased.

Figure 24:
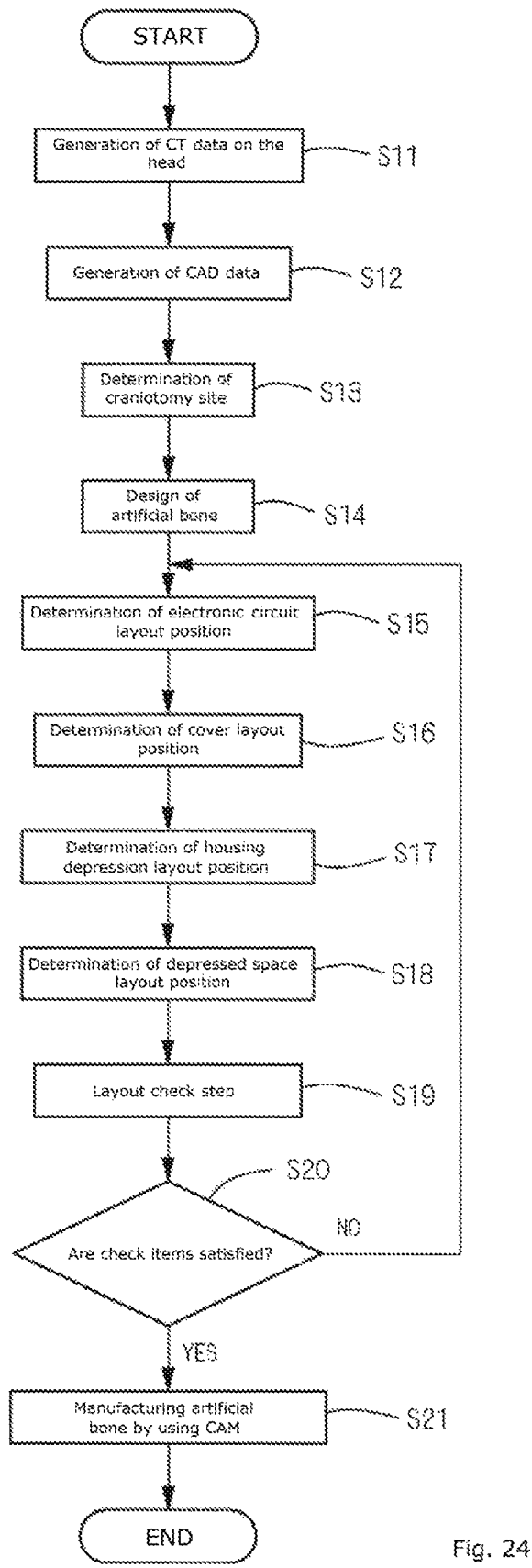
FIG. 24 is a flowchart showing a method for manufacturing a casing of an implantable device.

FIG. 24 shows a method for manufacturing the casing 16 of the implantable device 4 according to the third embodiment. First, a thin slice CT test is conducted on the patient, and detailed CT data on the head of the patient is generated (S11). Then, CAD data is generated by converting the CT data into CAD data (S12). Note that if the CT data can be handled using CAD, step S12 is not required. Subsequently, the craniotomy site 26 is determined using CAD, considering various elements such as the functional anatomy of the brain, the position of the affected site, the layout position of the sheet-shaped grid electrode array 2, and the state of the skull 29 (S13: craniotomy site determination step, see FIG. 9) and then the external shape of the artificial bone 28 (casing 16) matching the shape of the resected skull at the craniotomy site 26 is designed (S14: artificial bone design step). Specifically, considering such as the thickness dimension of the resected skull 27 and the thickness dimension of the convexity included in the artificial bone 28, the shape of the artificial bone 28 (casing 16) is determined in such a manner that it matches the shape of the resected skull 27. Thus, the external shape of the convexity 60 is roughly determined.

Next, the layout position of the electronic circuit 15 in the convexity 60 is determined (S15: electronic circuit layout position determination step). Here, the layout position of the electronic circuit 15 in the convexity 60 is determined while changing the bending angle of the electronic circuit 15. In this step, attention is paid not to excessively reduce the distance dimension between the top end surfaces of the IC chips 17 and the outer surface 601 of the convexity 60. This is because if there is a portion where the thickness dimension of the convexity 60 located above the housing depression 61 is extremely reduced, the impact resistance of the artificial bone 28 is reduced. This is also because if the thickness dimension of the convexity 60 located above the housing depression 61 is too small, it is difficult to perform cutting processing on a titanium block.

Next, the shape of the cover plate 70 is determined in such a manner that it matches the layout position of the electronic circuit 15 (S16: cover layout position determination step). If the electronic circuit 15 has an inverted V-shaped bent posture, the top surface shape of the cover plate 70 is determined in accordance with the bend angle. Next, the housing depression 61 in the convexity 60 is determined in such a manner that it can house the entire electronic circuit 15 including the molded portion 151 (S17: housing depression layout position determination step). Subsequently, the layout of the depressed space 63 is determined in such a manner that it matches the cover plate 70 (S18: depressed space layout position determination step). The positions of the cable channels 6464 are also determined in the depressed space layout position step).

Subsequently, the process proceeds to S19 to perform an entire layout check step. In this layout check step (S19), it is again checked whether the thickness dimension above the housing depression 61 of the convexity 60 is a predetermined thickness dimension. It is also checked that a predetermined height dimension is secured between the bottom surface of the periphery of the cover plate 70 and the inner surface 603 of the convexity 60. It is also checked whether the cables 3, 5 can be connected to the connectors 21, 22 mounted on the circuit boards 181, 182.

If it is determined in the check step S19 that any check item is not met (NO in S20), the process returns to S15 to reconsider the layout position of the electronic circuit 15, as well as reconsider such as the shapes of the housing depression 61 and the depressed space 62 (S16 to S18). Alternatively, the process may return to S14 to swell out the convexity 60 slightly outwardly.

If the items are satisfied in the check step S19 (YES in S20), the design of the artificial bone 28 (casing 16) is completed, and the cutting processing process of the artificial bone 28 is generated using CAM on the basis of the designed CAD data (S21). Specifically, cutting processing is performed on a titanium block to cut out the convexity 60 and the cover plate 70. The artificial bone 28 is also able to be manufactured using 3D printing technology such as selective laser melting method, direct metal laser sintering method and the like, based on CAD data. Subsequently, the electronic circuit 15 is mounted on the cover plate 70 and molded using a sealing resin. Then, the electronic circuit 15 is housed in the housing depression 61 along with the cover plate 70. The cover plate 70 is welded and fixed to the periphery of the aperture of the housing depression 61. Thus, the implantable device 4 is completed.

In a surgery, a craniotomy is correctly performed on the craniotomy site 26 determined in the above-mentioned craniotomy site determination step (S13) with the aid of a neurosurgical navigation system. The sheet-shaped grid electrode array 2 is placed on the brain 13 (on the cerebral cortex). The implantable device 4 is then placed within the craniotomy site 26 and fixed to the skull 29 using the set screws 37 to fill the craniotomy site 26.

DESCRIPTION OF SIGNS

2 function unit (sheet-shaped grid electrode array)
3 cable (analog cable)
4 implantable device
15 electronic circuit
16 casing
17 semiconductor chip (IC chip)
18 circuit board
19 flexible printed wiring
23 screw
24 hole
26 craniotomy site
27 resected skull
28 artificial bone
30 outer convexity surface
31 inner convexity side
32 internal space
60 convexity
601 outer surface
602 side surface
603 inner surface
61 housing depression
611 side surface of housing depression
63 depressed space
631 receiving surface of depressed space
632 side surface of depressed space
70 cover plate

What is claimed is:

1. An implantable device connected to a functional unit implanted in a human head via a cable, comprising:
    an electronic circuit; and
    a casing enclosing the electronic circuit, wherein the casing comprises an outer convexity surface configured to be flush with an external top shape of a resected skull related to at least a craniotomy site of an artificial bone designed in accordance with a skull shape of a person in order to fill the craniotomy site,
    wherein the electronic circuit is configured to receive measured signals transmitted by the functional unit and control the functional unit,
    wherein an entirety of the electronic circuit is disposed inside the casing,
    wherein the functional unit comprises a sheet-shaped grid electrode array configured to be disposed under a dural membrane and attach to a surface of a brain of the human head,
    wherein the cable is configured to penetrate the dural membrane,
    wherein the casing is disposed above the dural membrane,
    wherein the electronic circuit within the casing and the sheet-shaped grid electrode array are configured to connect with each other via the cable penetrating the dural membrane,
    wherein the casing comprises an inner convexity surface matching an internal shape of the resected skull, and internal space formed between the outer convexity surface and the inner convexity surface, wherein the electronic circuit is fixed in the internal space,
    wherein the electronic circuit comprises two or more circuit boards and a flexible printed wiring electrically connecting the circuit boards, and
    wherein the two or more circuit boards are positioned adjacent to each other in an in-plane direction of the casing and bendable around a connection made by the flexible printed wiring, such that the two or more circuit boards are fixed adaptably to the inner convexity surface.

2. The implantable device according to claim 1, wherein
    a hole for a screw is formed on a circuit board included in the electronic circuit, and
    a fixing boss for fixing the circuit board using a screw is formed on one of the outer convexity surface and the inner convexity surface in a manner protruding toward an interior of the artificial bone.

3. The implantable device according to claim 1, wherein
    a through hole for a screw is formed on each of the two or more circuit boards, and
    each circuit board is fixed to the fixing boss using a screw, the fixing boss being formed on one of the outer convexity surface and the inner convexity surface in a protruding manner.

4. The implantable device according to claim 1, wherein the two or more circuit boards are spaced apart from one another along the in-plane direction.

* * * * *